United States Patent
Gitai et al.

(10) Patent No.: US 11,077,109 B2
(45) Date of Patent: *Aug. 3, 2021

(54) COMPOUNDS HAVING ANTIBACTERIAL ACTIVITY AND METHODS OF USE

(71) Applicant: The Trustees of Princeton University, Princeton, NJ (US)

(72) Inventors: Zemer Gitai, Princeton, NJ (US); James Martin, Princeton, NJ (US); Hsin-Jung Li, Princeton, NJ (US); Max Wilson, Princeton, NJ (US); Hahn Kim, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/052,212

(22) Filed: Aug. 1, 2018

(65) Prior Publication Data
US 2019/0201401 A1    Jul. 4, 2019

Related U.S. Application Data

(60) Provisional application No. 62/539,886, filed on Aug. 1, 2017.

(51) Int. Cl.
*A61K 31/517* (2006.01)
*A61P 31/04* (2006.01)
*A61P 35/00* (2006.01)
*A61K 31/519* (2006.01)

(52) U.S. Cl.
CPC .......... *A61K 31/517* (2013.01); *A61K 31/519* (2013.01); *A61P 31/04* (2018.01); *A61P 35/00* (2018.01)

(58) Field of Classification Search
CPC ...... A61K 31/517; A61K 31/519; A61P 31/04
USPC ........................................................ 514/210
See application file for complete search history.

(56) References Cited

U.S. PATENT DOCUMENTS

| | | | | |
|---|---|---|---|---|
| 8,877,710 | B2 * | 11/2014 | Johansson | A61P 11/00 514/13.9 |
| 9,381,243 | B2 * | 7/2016 | Johansson | A61P 35/02 |
| 9,480,259 | B2 * | 11/2016 | Witschel | C07D 311/94 |
| 10,077,273 | B2 * | 9/2018 | Rabinowitz | A61K 31/19 |
| 10,611,798 | B2 * | 4/2020 | Bar-Shavit | C07K 7/06 |
| 2011/0268732 | A1 * | 11/2011 | Johansson | A61P 39/02 424/133.1 |

* cited by examiner

*Primary Examiner* — Tracy Vivlemore
*Assistant Examiner* — Ebenezer O Sackey
(74) *Attorney, Agent, or Firm* — J. Clinton Wimbish; Nexsen Pruet, PLLC

(57) ABSTRACT

In one aspect, methods of treating bacterial infections are described herein employing compounds having more than one target for antibacterial activity. Additionally pharmaceutical compositions comprising such compounds are also described.

14 Claims, 37 Drawing Sheets

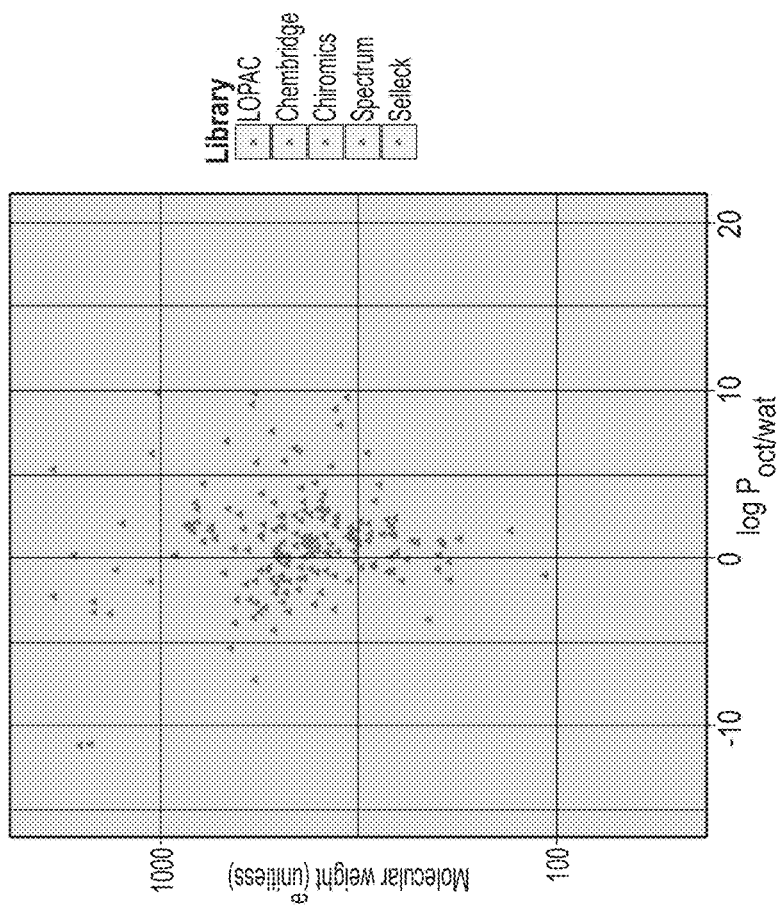
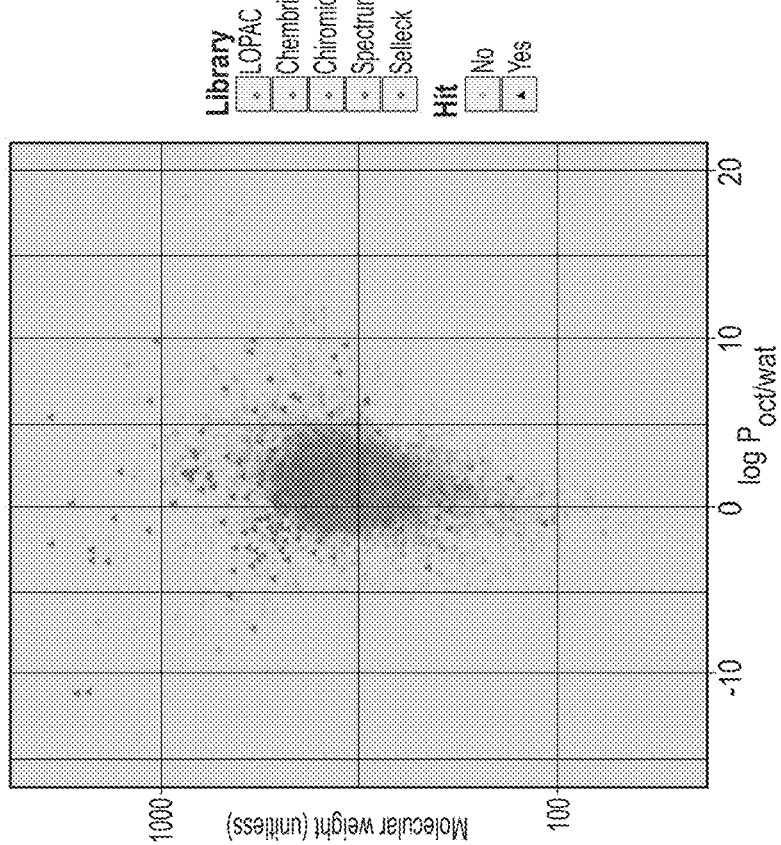
FIGURE 2(B)
FIGURE 2(A)

| | Dilutions until resistance seen |
|---|---|
| SCH 79797 | No resistance |
| Trimethoprim | 3 |
| Ampicillin | 3 |

FIGURE 10(B)

COMPOUNDS HAVING ANTIBACTERIAL ACTIVITY AND METHODS OF USE

RELATED APPLICATION DATA

The present application claims priority pursuant to 35 U.S.C. § 119(e) to U.S. Provisional Patent Application Ser. No. 62/539,886 filed Aug. 1, 2017, which is incorporated herein by reference in its entirety.

FIELD

The present invention relates to antibacterial compounds and, in particular, to antibacterial compounds inhibiting antibacterial resistance via multiple modes of action.

BACKGROUND

The discovery of penicillin in 1929 ushered in the 'Golden Age' of antibiotic discovery and with it, over the next three decades, more than twenty unique classes of antibiotics. The discovery and development of these lifesaving molecules has been in serious decline. Since the end of the 'Golden Age' in 1962 only two orally available antibiotics with completely novel targets, linezolid and a daptomycin, have been brought to the market. Declining rates of antibiotic discovery would be unalarming if it were not for evolution's perpetual offensive, constantly selecting antibiotic resistant bacteria through horizontal gene transfer and spontaneous mutation. In the United States alone, this manifests in a record 2 million antibiotic resistant infections, which annually kill 23,000 people. Moreover, such infections have been estimated to cost our health system as much as $35 billion annually. Other than better antibiotic stewardship, which has been shown to decrease the rate of hospital acquired infections, the only way to combat bacterial infections is to continuously develop antibiotics and other therapeutics with novel mechanisms of action (MOA), which have yet to slip into obsolescence.

SUMMARY

In one aspect, methods of treating bacterial infections are described herein. In some embodiments, for example, a method comprises administering to a patient having a bacterial infection a therapeutically effective amount of one or more compounds of Formula (I) and/or salt(s) thereof:

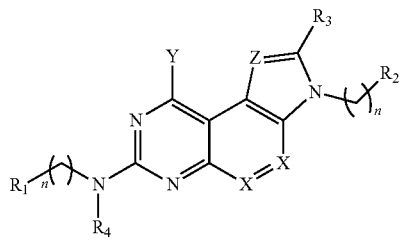

(I)

wherein $R_1$-$R_4$ are independently selected from the group consisting of hydrogen, alkyl, alkenyl, heteroalkyl, cycloalkyl, heterocycloalkyl, aryl, heteroaryl, alkyl-aryl, alkyl-heteroaryl, amide, sulfonamide, and urea, wherein the alkyl, alkenyl, heteroalkyl, cycloalkyl, heterocycloalkyl, aryl, heteroaryl, alkyl-aryl, alkyl-heteroaryl, amide and sulfonamide are optionally substituted with one or more substituents selected from the group consisting of $(C_1$-$C_{10})$-alkyl, $(C_1$-$C_{10})$-alkenyl, cycloalkyl, heterocycloalkyl, aryl, heteroaryl, alkoxy, amide, sulfonamide, urea, halo, hydroxy, $C(O)OR_5$, and $C(O)R_6$, wherein $R_5$ is selected from the group consisting of hydrogen, alkyl and alkenyl and $R_6$ is selected from the group consisting of hydrogen, alkyl, alkenyl, heteroalkyl, cycloalkyl, heterocycloalkyl, aryl, heteroaryl and $NR_7R_8$, wherein $R_7$ and $R_8$ are independently selected from the group consisting of hydrogen, alkyl, alkenyl, aryl and heteroaryl; and wherein X and Z are independently selected from the group consisting of C, N and O; and wherein Y is selected from the group consisting of OH and $NR_9R_{10}$, wherein $R_9$ and $R_{10}$ are independently selected from the group consisting of hydrogen, alkyl, heteroalkyl, cycloalkyl, heterocycloalkyl, alkenyl, aryl, heteroaryl, amide, sulfonamide, urea and $C(O)R_{11}$ wherein $R_{11}$ is selected from the group consisting of hydrogen, alkyl, alkenyl, heteroalkyl, cycloalkyl, heterocycloalkyl, aryl and heteroaryl and wherein $R_9$ and $R_{10}$ may optionally form a ring structure; and n is an integer from 0 to 5.

In another aspect, a method comprises administering to a patient having a bacterial infection a therapeutically effective amount of one or more compounds of Formula (II) and/or salt(s) thereof:

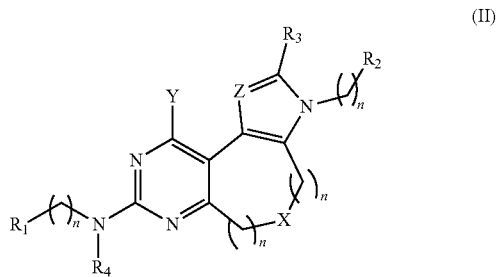

(II)

wherein $R_1$-$R_4$ are independently selected from the group consisting of hydrogen, alkyl, alkenyl, heteroalkyl, cycloalkyl, heterocycloalkyl, aryl, heteroaryl, alkyl-aryl, alkyl-heteroaryl, amide, sulfonamide, and urea, wherein the alkyl, alkenyl, heteroalkyl, cycloalkyl, heterocycloalkyl, aryl, heteroaryl, alkyl-aryl, alkyl-heteroaryl, amide and sulfonamide are optionally substituted with one or more substituents selected from the group consisting of $(C_1$-$C_{10})$-alkyl, $(C_1$-$C_{10})$-alkenyl, cycloalkyl, heterocycloalkyl, aryl, heteroaryl, alkoxy, amide, sulfonamide, urea, halo, hydroxy, $C(O)OR_5$, and $C(O)R_6$, wherein $R_5$ is selected from the group consisting of hydrogen, alkyl and alkenyl and $R_6$ is selected from the group consisting of hydrogen, alkyl, alkenyl, heteroalkyl, cycloalkyl, heterocycloalkyl, aryl, heteroaryl and $NR_7R_8$, wherein $R_7$ and $R_8$ are independently selected from the group consisting of hydrogen, alkyl, alkenyl, aryl and heteroaryl; and wherein X is selected from the group consisting of $CR_9R_{10}$, O, S, $SO_2$, and $NR_{11}R_{12}$, and wherein Y is selected from the group consisting of OH and $NR_{13}R_{14}$, wherein $R_9$-$R_{14}$ are independently selected from the group consisting of hydrogen, alkyl, heteroalkyl, cycloalkyl, heterocycloalkyl, alkenyl, aryl, heteroaryl, amide, sulfonamide, urea and $C(O)R_{15}$ wherein $R_{15}$ is selected from the group consisting of hydrogen, alkyl, alkenyl, heteroalkyl, cycloalkyl, heterocycloalkyl, aryl and heteroaryl and wherein $R_{13}$ and $R_{14}$ may optionally form a ring structure; and n is an integer from 0 to 5; and wherein Z is independently selected from the group consisting of C and N; and n is an integer from 0 to 5.

In another aspect, pharmaceutical compositions are described herein. In some embodiments, the pharmaceutical compositions are operable for treating bacterial infections and/or cancerous tissue. A pharmaceutical composition, in some embodiments, comprises a compound of Formula (I) and/or salt thereof:

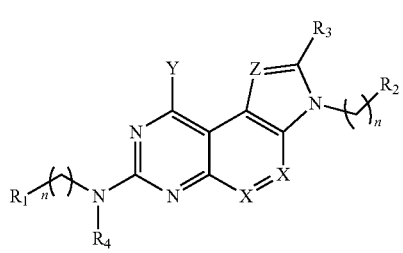

(I)

wherein $R_1$-$R_4$ are independently selected from the group consisting of hydrogen, alkyl, alkenyl, heteroalkyl, cycloalkyl, heterocycloalkyl, aryl, heteroaryl, alkyl-aryl, alkyl-heteroaryl, amide, sulfonamide, and urea, wherein the alkyl, alkenyl, heteroalkyl, cycloalkyl, heterocycloalkyl, aryl, heteroaryl, alkyl-aryl, alkyl-heteroaryl, amide and sulfonamide are optionally substituted with one or more substituents selected from the group consisting of $(C_1$-$C_{10})$-alkyl, $(C_1$-$C_{10})$-alkenyl, cycloalkyl, heterocycloalkyl, aryl, heteroaryl, alkoxy, amide, sulfonamide, urea, halo, hydroxy, $C(O)OR_5$, and $C(O)R_6$, wherein $R_5$ is selected from the group consisting of hydrogen, alkyl and alkenyl and $R_6$ is selected from the group consisting of hydrogen, alkyl, alkenyl, heteroalkyl, cycloalkyl, heterocycloalkyl, aryl, heteroaryl and $NR_7R_8$, wherein $R_7$ and $R_8$ are independently selected from the group consisting of hydrogen, alkyl, alkenyl, aryl and heteroaryl; and wherein X and Z are independently selected from the group consisting of C, N and O; and wherein Y is selected from the group consisting of OH and $NR_9R_{10}$, wherein $R_9$ and $R_{10}$ are independently selected from the group consisting of hydrogen, alkyl, heteroalkyl, cycloalkyl, heterocycloalkyl, alkenyl, aryl, heteroaryl, amide, sulfonamide, urea and $C(O)R_{11}$ wherein $R_{11}$ is selected from the group consisting of hydrogen, alkyl, alkenyl, heteroalkyl, cycloalkyl, heterocycloalkyl, aryl and heteroaryl and wherein $R_9$ and $R_{10}$ may optionally form a ring structure; and n is an integer from 0 to 5.

In other embodiments, a pharmaceutical composition comprises a compound of Formula (II) and/or salt thereof:

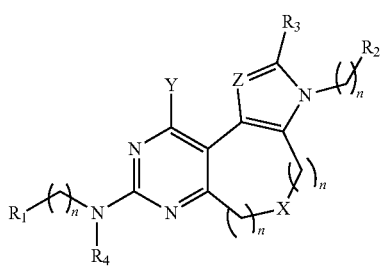

(II)

wherein $R_1$-$R_4$ are independently selected from the group consisting of hydrogen, alkyl, alkenyl, heteroalkyl, cycloalkyl, heterocycloalkyl, aryl, heteroaryl, alkyl-aryl, alkyl-heteroaryl, amide, sulfonamide, and urea, wherein the alkyl, alkenyl, heteroalkyl, cycloalkyl, heterocycloalkyl, aryl, heteroaryl, alkyl-aryl, alkyl-heteroaryl, amide and sulfonamide are optionally substituted with one or more substituents selected from the group consisting of $(C_1$-$C_{10})$-alkyl, $(C_1$-$C_{10})$-alkenyl, cycloalkyl, heterocycloalkyl, aryl, heteroaryl, alkoxy, amide, sulfonamide, urea, halo, hydroxy, $C(O)OR_5$ and $C(O)R_6$, wherein $R_5$ is selected from the group consisting of hydrogen, alkyl and alkenyl and $R_6$ is selected from the group consisting of hydrogen, alkyl, alkenyl, heteroalkyl, cycloalkyl, heterocycloalkyl, aryl, heteroaryl and $NR_7R_8$, wherein $R_7$ and $R_8$ are independently selected from the group consisting of hydrogen, alkyl, alkenyl, aryl and heteroaryl; and wherein X is selected from the group consisting of $CR_9R_{10}$, O, S, $SO_2$, and $NR_{11}R_{12}$, and wherein Y is selected from the group consisting of OH and $NR_{13}R_{14}$, wherein $R_9$-$R_{14}$ are independently selected from the group consisting of hydrogen, alkyl, heteroalkyl, cycloalkyl, heterocycloalkyl, alkenyl, aryl, heteroaryl, amide, sulfonamide, urea and $C(O)R_{15}$ wherein $R_{15}$ is selected from the group consisting of hydrogen, alkyl, alkenyl, heteroalkyl, cycloalkyl, heterocycloalkyl, aryl and heteroaryl and wherein $R_{13}$ and $R_{14}$ may optionally form a ring structure; and n is an integer from 0 to 5; and wherein Z is independently selected from the group consisting of C and N; and n is an integer from 0 to 5.

In another aspect, methods of treating bacterial infections are described herein employing compounds previously unknown to exhibit antibacterial activity. Identification and screening of prior compounds for novel MOAs can greatly facilitate the development of new treatments at a time when bacterial species are exhibiting greater recalcitrance to current treatment options. For example, method comprises administering to a patient having a bacterial infection a therapeutically effective amount of a composition including an antibacterial agent selected from the group consisting of DL-erythro-dihydrosphingosine, N3-Cyclopropyl-7-[[4-(1-methylethyl)phenyl]methyl]-7H-pyrrolo[3,2-F]quinazoline-1,3-diamine dihydrochloride (SCH 79797), 3-(3,5-dibromo-4-hydroxybenzyliden)-5-iodo-1,3-dihydroindol-2-one (GW5074), 2-(p-amylcinnamoyl)amino-4-chlorobenzoic acid (ONO-RS-82), 2-[3-(1,3-dihydro-1,3,3-trimethyl-2H-indol-2-ylidene)-1-propenyl]-3-ethyl-benzothiazolium iodide (AC-93253 iodide), 1-[bis(4-Chlorophenyl)methyl]-3-[2-(2,4-dichlorophenyl)-2-(2,4-dichlorobenzyloxy)ethyl]-1H-imidazolium chloride (Calmidazolium chloride), N,N-dimethyl-3-[2-(trifluoromethyl)phenothiazin-10-yl]propan-1-amine (Triflupromazine), N-[2-(p-Bromocinnamylamino)ethyl]-5-isoquinolinesulfonamide dihydrochloride (H-89-2HCl), (S)-5-Chloro-N-((2-oxo-3-(4-(3-oxomorpholino)phenyl)oxazolidin-5-yl)methyl)thiophene-2-carboxamide (Rivaroxaban), 1-[(2R,4S,5S)-4-azido-5-(hydroxymethypoxolan-2-yl]-5-methylpyrimidine-2,4-dione (AZT) and CP000294 and salts and derivatives thereof.

In some embodiments, the antibacterial agent is present in the composition at a minimum inhibitory concentration (MIC) of less than 1 μg/ml. In other embodiments, the antibacterial agent is present at a MIC of 0.1 to 10 μg/ml. Moreover, in some embodiments, antibacterial activity of one or more compounds described herein can be associated with disruption of one or more bacterial metabolic pathways. For example, one or more compounds may interfere with or disrupt the folate biosynthetic pathway.

In another aspect, methods of treating cancer are described herein. In some embodiments, a method comprises administering to a patient having cancer a therapeutically effective amount of a composition comprising a compound of Formula (I) and/or Formula (II) and/or salt(s) thereof. Anticancer activity of compounds of Formula (I)

and/or Formula (II), in some embodiments, is associated with disruption of the folate biosynthetic pathway employed by the cancer cells. FIG. 17, for example, illustrates anticancer activity of a compound described herein for breast cancer cells.

These and other embodiments are described further in the following detailed description.

BRIEF DESCRIPTION OF THE DRAWINGS

FIG. 2(A) illustrates compounds in the primary screen shaded by library and arranged according to their molecular weight and predicted log partitioning coefficient between octanol and water, a measure of hydrophobicity.

FIG. 2(B) illustrates only the compounds that inhibited bacterial growth displayed on the exact same scale as in FIG. 2(A).

FIG. 10(B) provides number of dilutions into sub-lethal and lethal doses of drug that were required until growth in lethal doses of antibiotic was observed.

DETAILED DESCRIPTION

Figure 1:
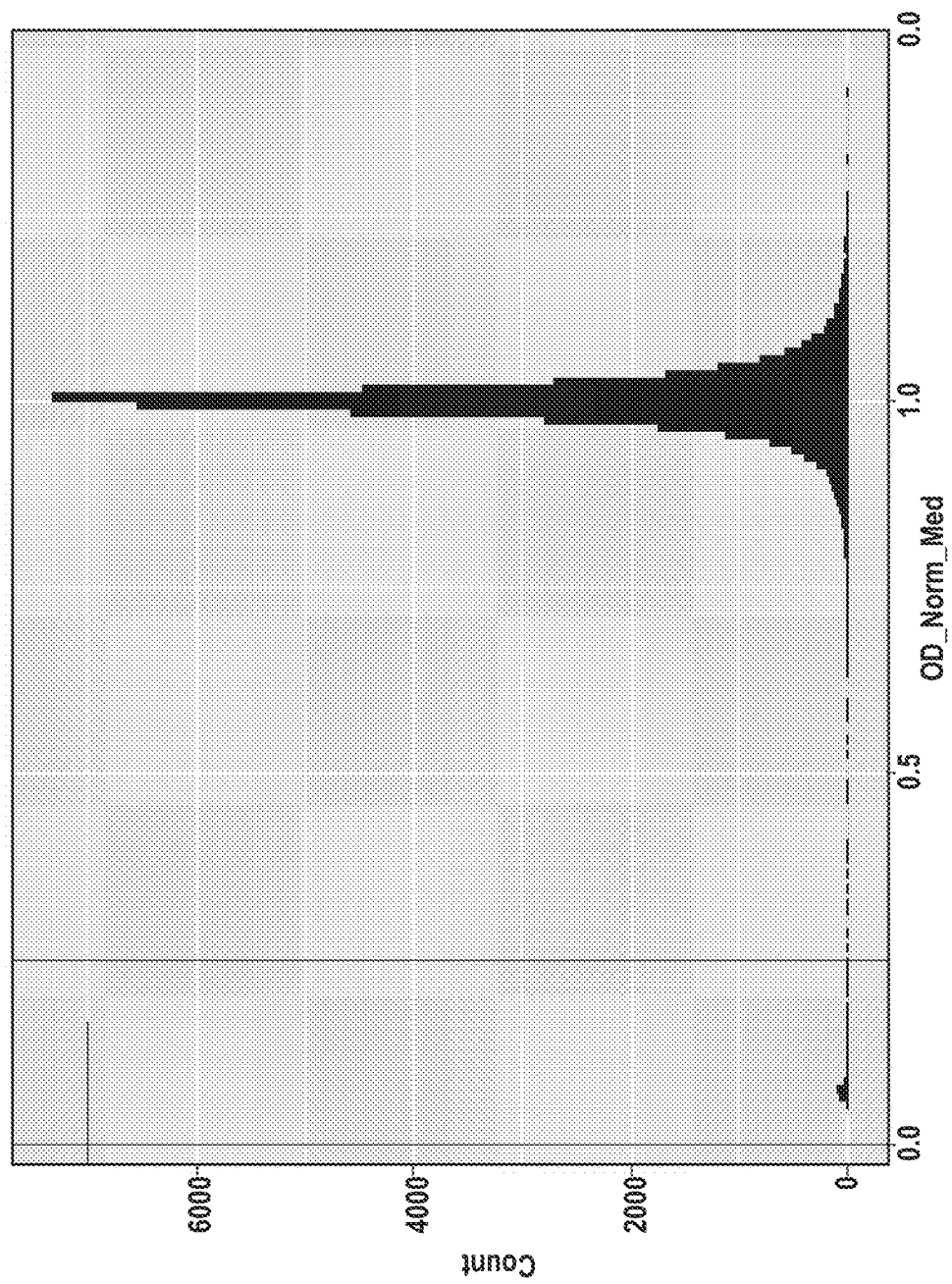
FIG. 1 illustrates median-normalized optical density (OD600) of the imp strain grown for 24 hours in terrific broth.
Figure 3A:
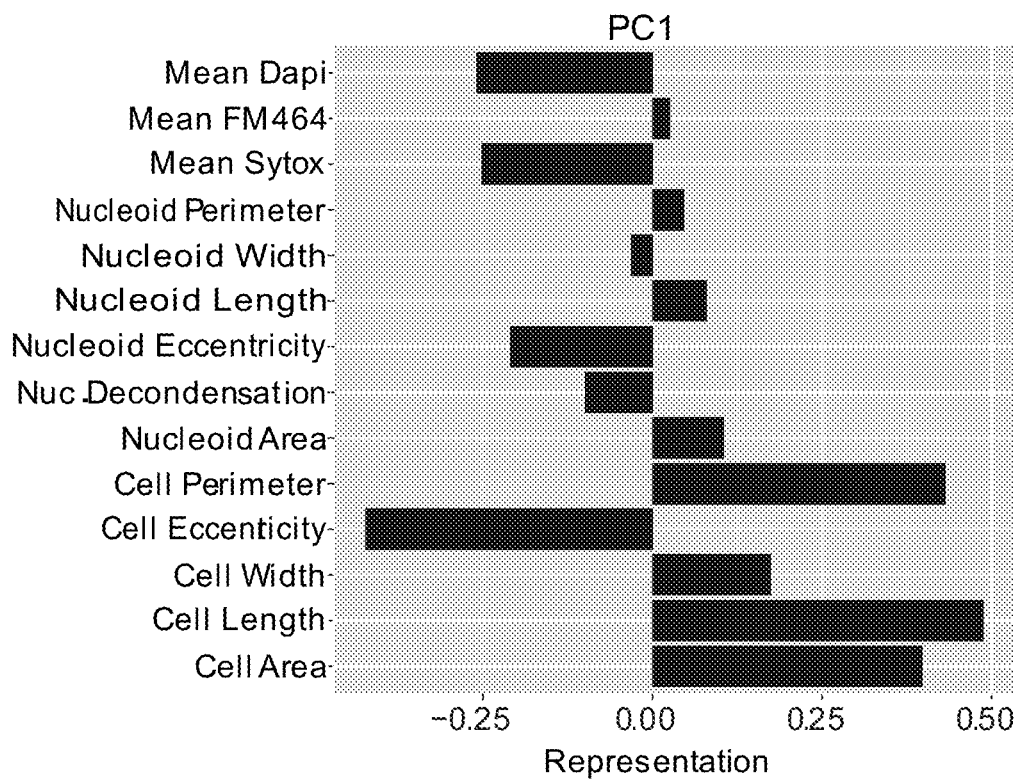
FIGS. 3(A) through 3(D) illustrate loadings on the first 4 principle components for simple averages dimensional reduction scheme.
Figure 3B:
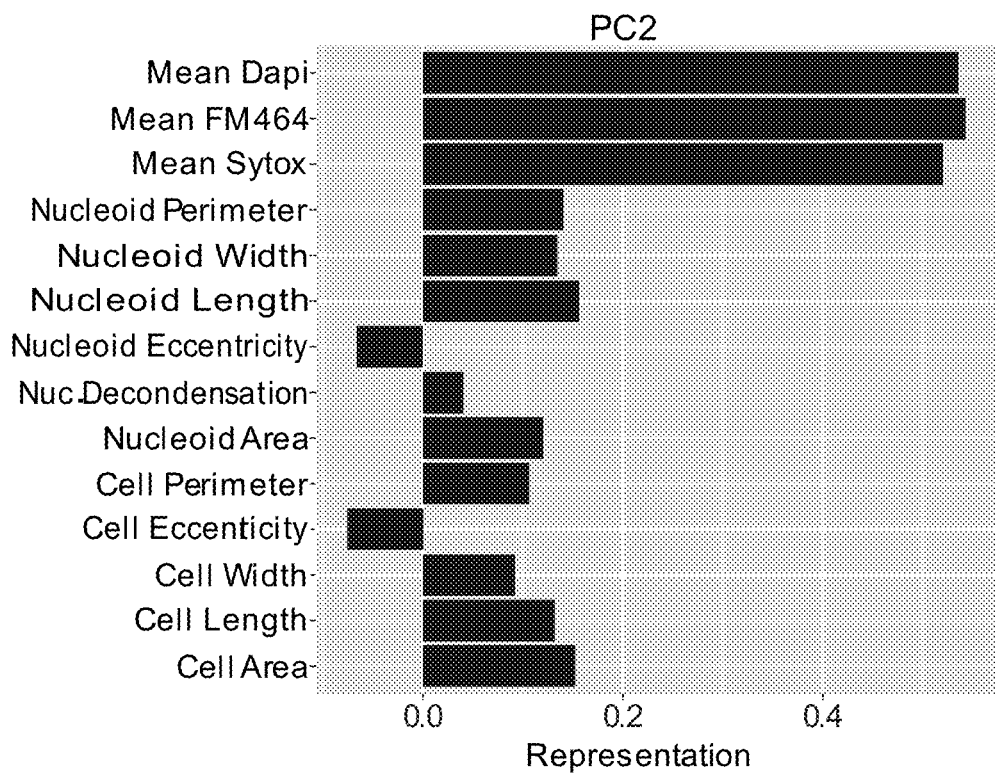
Figure 3C:
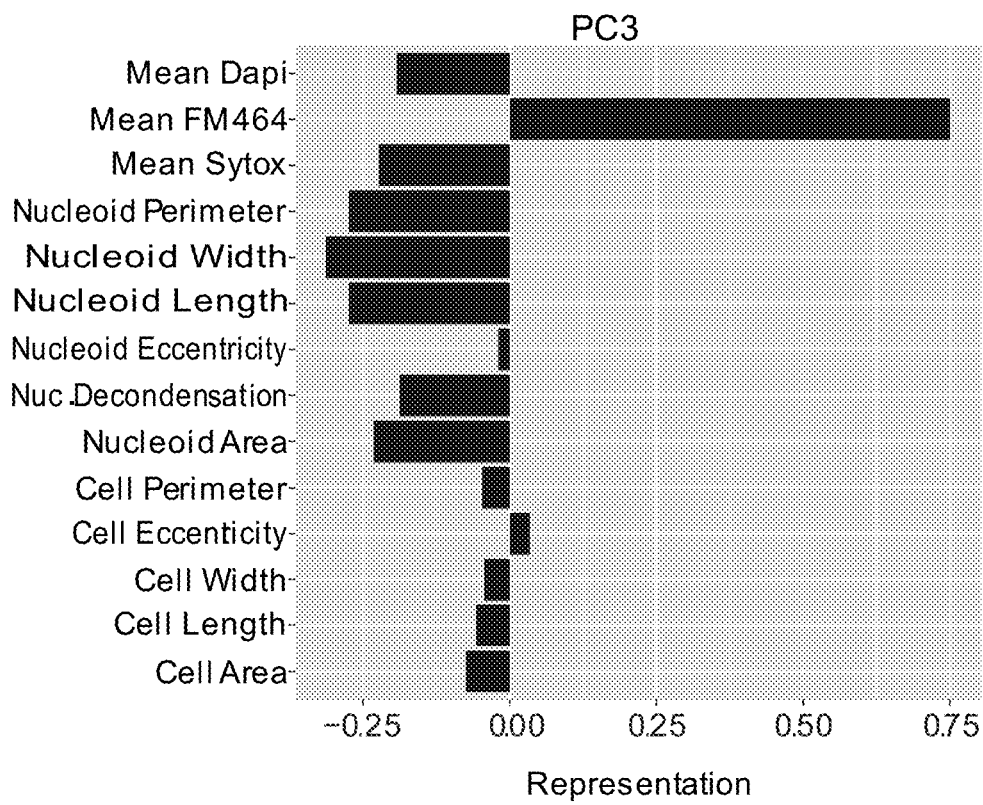
Figure 3D:
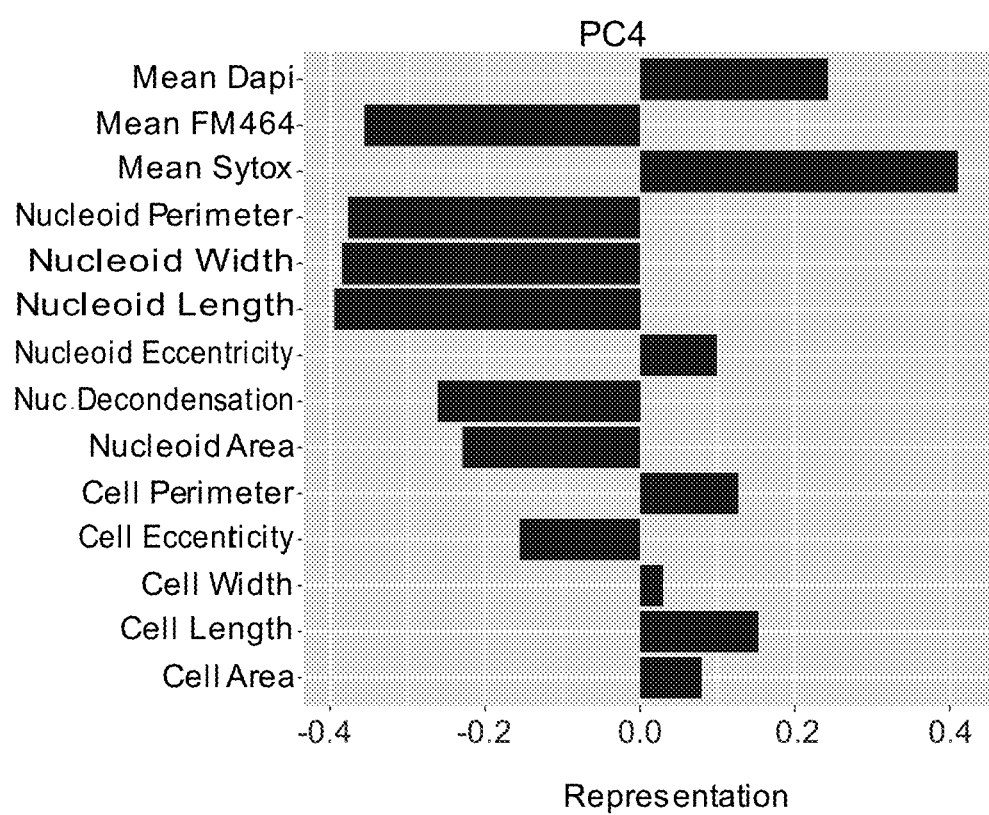
Figure 4A:
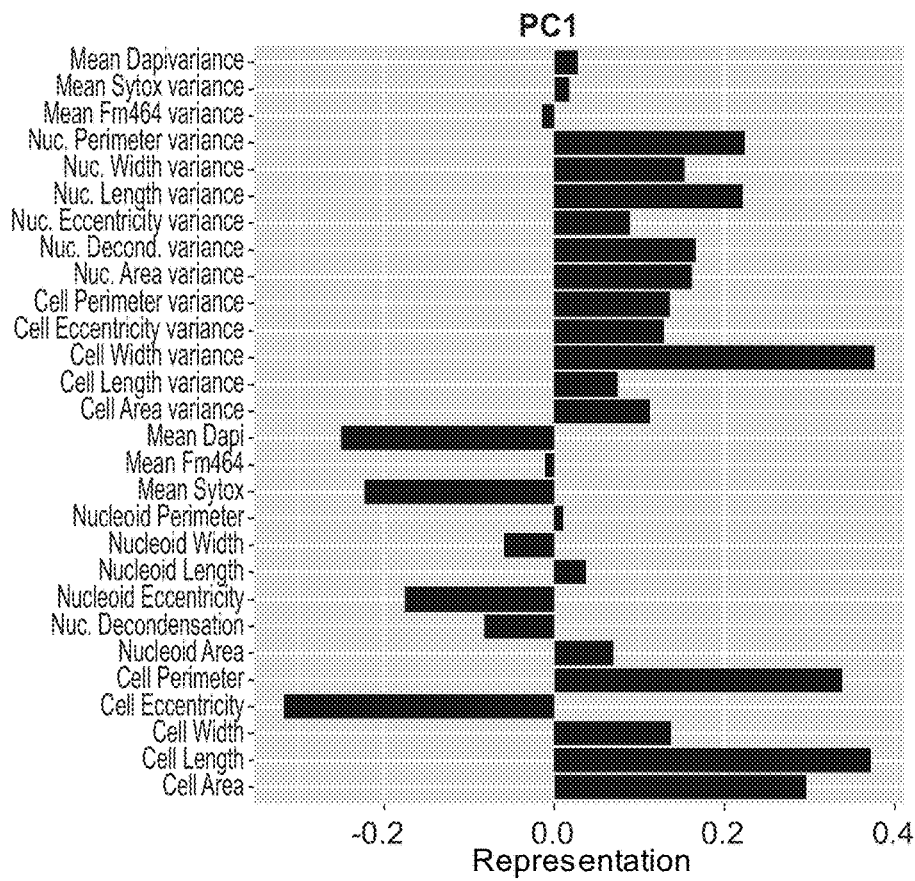
FIGS. 4(A) through 4(F) illustrate loadings on the first 6 principle components for combined averages and variances dimensional reduction scheme.
Figure 4B:
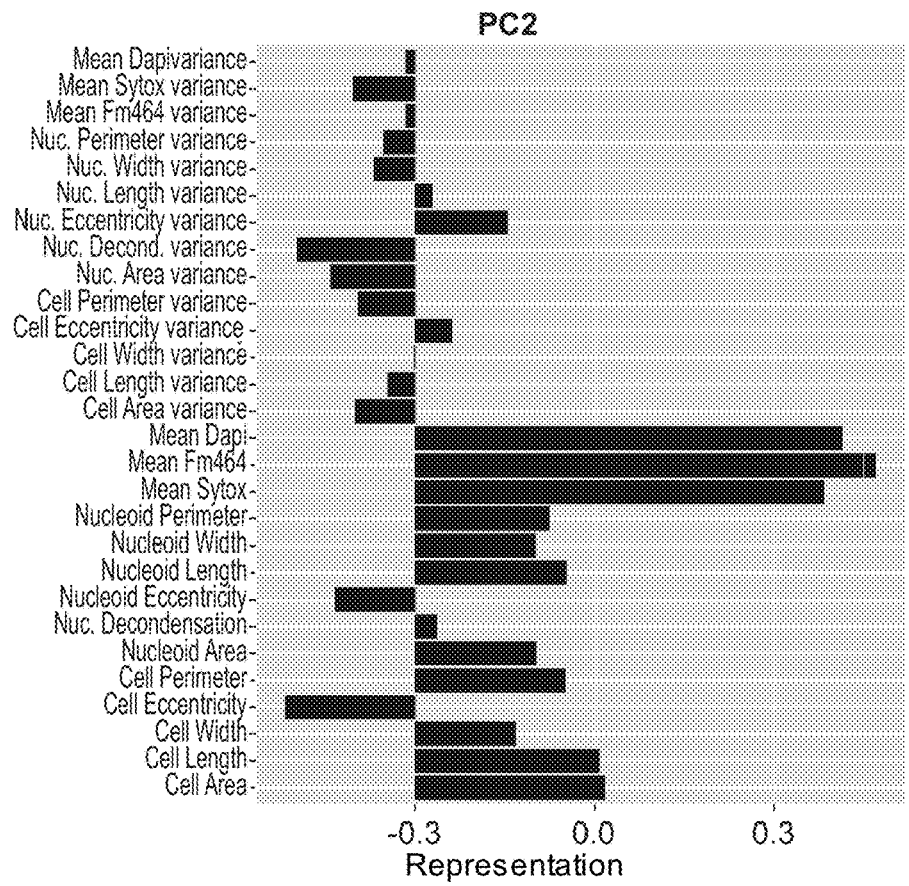
Figure 4C:
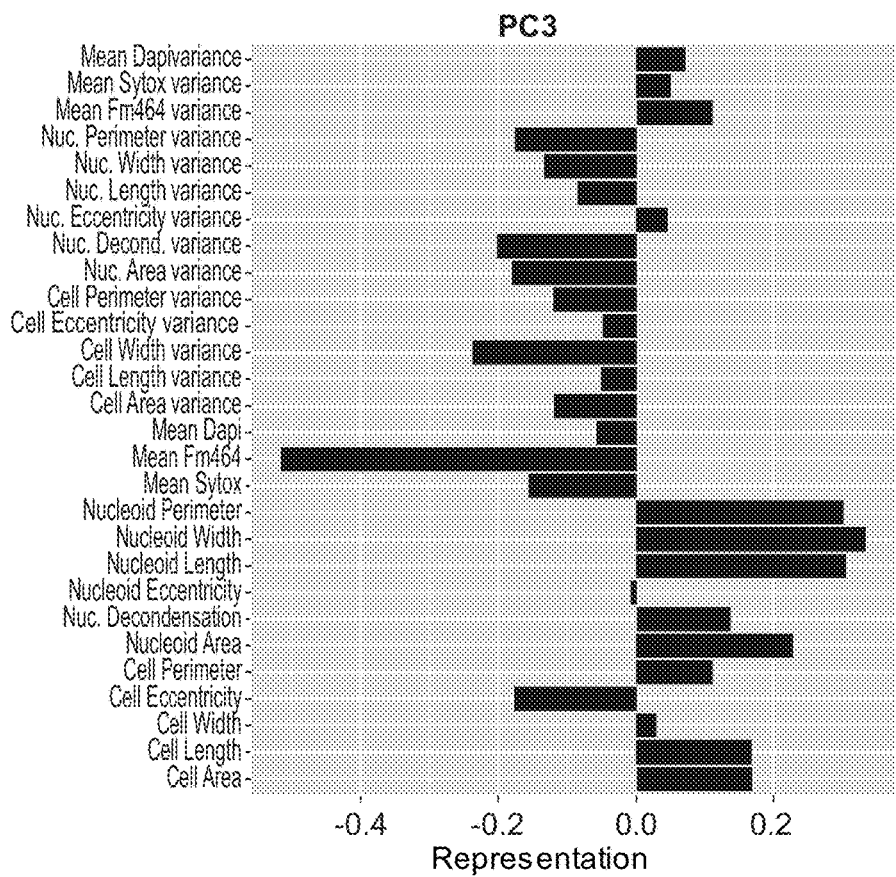
Figure 4D:
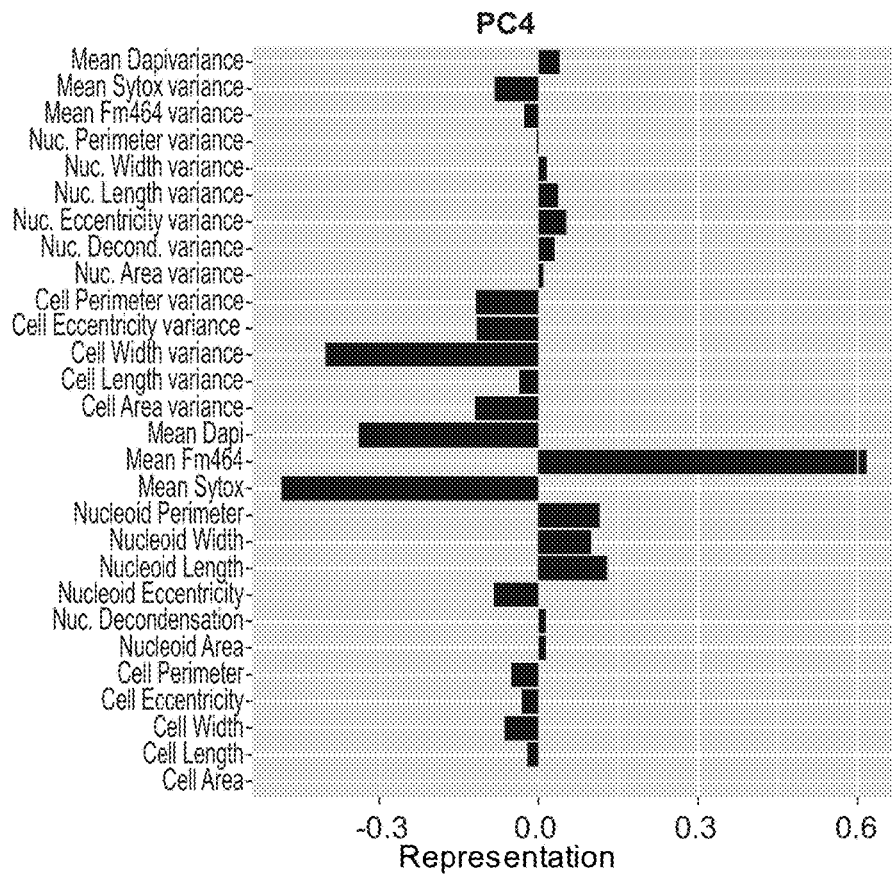
Figure 4E:
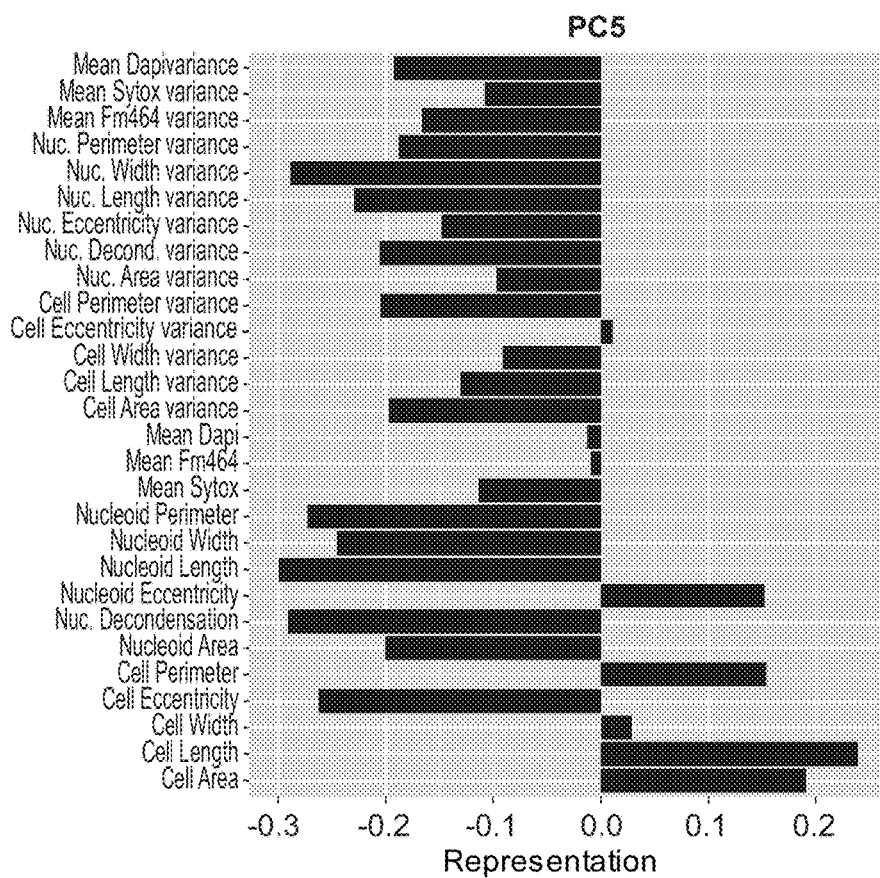
Figure 4F:
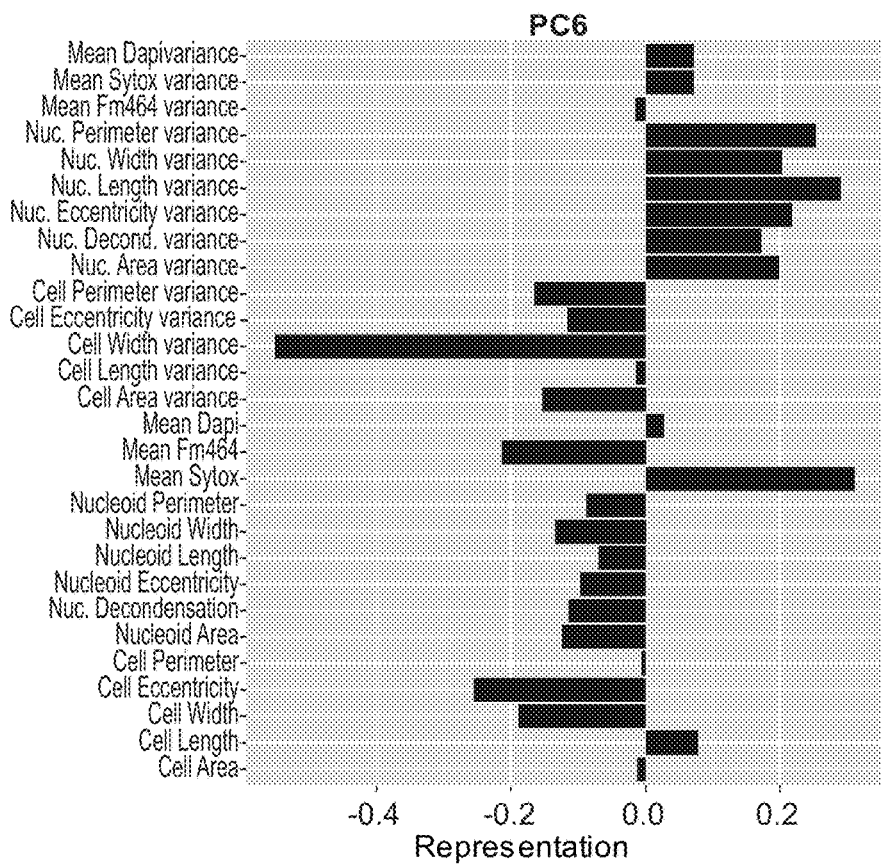

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

Definitions

The term "alkyl" as used herein, alone or in combination, refers to a straight or branched saturated hydrocarbon group optionally substituted with one or more substituents. For example, an alkyl can be $C_1$-$C_{30}$ or $C_1$-$C_{18}$.

The term "alkenyl" as used herein, alone or in combination, refers to a straight or branched chain hydrocarbon group having at least one carbon-carbon double bond and optionally substituted with one or more substituents The term "aryl" as used herein, alone or in combination, refers to an aromatic monocyclic or multicyclic ring system optionally substituted with one or more ring substituents.

The term "heteroaryl" as used herein, alone or in combination, refers to an aromatic monocyclic or multicyclic ring system in which one or more of the ring atoms is an element other than carbon, such as nitrogen, oxygen and/or sulfur.

The term "cycloalkyl" as used herein, alone or in combination, refers to a non-aromatic, mono- or multicyclic ring system optionally substituted with one or more ring substituents.

The term "heterocycloalkyl" as used herein, alone or in combination, refers to a non-aromatic, mono- or multicyclic ring system in which one or more of the atoms in the ring system is an element other than carbon, such as nitrogen, oxygen or sulfur, alone or in combination, and wherein the ring system is optionally substituted with one or more ring substituents.

The term "heteroalkyl" as used herein, alone or in combination, refers to an alkyl moiety as defined above, having one or more carbon atoms in the chain, for example one, two or three carbon atoms, replaced with one or more heteroatoms, which may be the same or different, where the point of attachment to the remainder of the molecule is through a carbon atom of the heteroalkyl radical.

The term "alkoxy" as used herein, alone or in combination, refers to the moiety RO—, where R is alkyl or alkenyl defined above.

The term "halo" as used herein, alone or in combination, refers to elements of Group VIIA of the Periodic Table (halogens). Depending on chemical environment, halo can be in a neutral or anionic state.

In one aspect, methods of treating bacterial infections are described herein. In some embodiments, for example, a method comprises administering to a patient having a bacterial infection a therapeutically effective amount of one or more compounds of Formula (I) and/or salt(s) thereof:

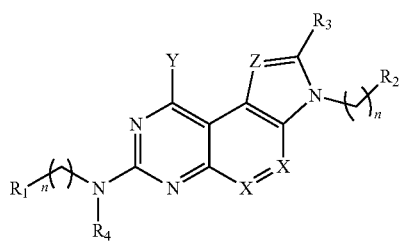

(I)

wherein $R_1$-$R_4$ are independently selected from the group consisting of hydrogen, alkyl, alkenyl, heteroalkyl, cycloalkyl, heterocycloalkyl, aryl, heteroaryl, alkyl-aryl, alkyl-heteroaryl, amide, sulfonamide, and urea, wherein the alkyl, alkenyl, heteroalkyl, cycloalkyl, heterocycloalkyl, aryl, heteroaryl, alkyl-aryl, alkyl-heteroaryl, amide and sulfonamide are optionally substituted with one or more substituents selected from the group consisting of $(C_1$-$C_{10})$-alkyl, $(C_1$-$C_{10})$-alkenyl, cycloalkyl, heterocycloalkyl, aryl, heteroaryl, alkoxy, amide, sulfonamide, urea, halo, hydroxy, $C(O)OR_5$, and $C(O)R_6$, wherein $R_5$ is selected from the group consisting of hydrogen, alkyl and alkenyl and $R_6$ is selected from the group consisting of hydrogen, alkyl, alkenyl, heteroalkyl, cycloalkyl, heterocycloalkyl, aryl, heteroaryl and $NR_7R_8$, wherein $R_7$ and $R_8$ are independently selected from the group consisting of hydrogen, alkyl, alkenyl, aryl and heteroaryl; and wherein X and Z are independently selected from the group consisting of C, N and O; and wherein Y is selected from the group consisting of OH and $NR_9R_{10}$, wherein $R_9$ and $R_{10}$ are independently selected from the group consisting of hydrogen, alkyl, heteroalkyl, cycloalkyl, heterocycloalkyl, alkenyl, aryl, heteroaryl, amide, sulfonamide, urea and $C(O)R_{11}$ wherein $R_{11}$ is selected from the group consisting of hydrogen, alkyl, alkenyl, heteroalkyl, cycloalkyl, heterocycloalkyl, aryl and heteroaryl and wherein $R_9$ and $R_{10}$ may optionally form a ring structure; and n is an integer from 0 to 5.

In some embodiments, one or more compounds of Formula (I) are of Formula (IA):

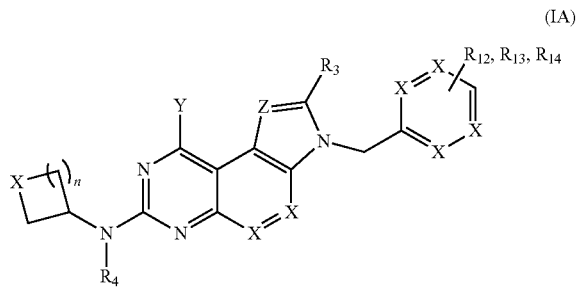

(IA)

wherein $R_3$, $R_4$, X, Y and Z and n are defined above and $R_{12}$-$R_{14}$ are independently selected from the group consisting of halo, alkyl, alkenyl, cycloalkyl, heterocycloalkyl, aryl, heteroaryl, alkoxy, amide, sulfonamide, urea, hydroxy, $C(O)OR_{15}$, and $C(O)R_{16}$, wherein $R_{15}$ is selected from the group consisting of hydrogen, alkyl and alkenyl and $R_{16}$ is independently selected from the group consisting of hydrogen, alkyl, alkenyl, heteroalkyl, cycloalkyl, heterocycloalkyl, aryl, heteroaryl and $NR_{17}R_{18}$, wherein $R_{17}$ and $R_{18}$ are independently selected from the group consisting of hydrogen and alkyl.

In another aspect, a method comprises administering to a patient having a bacterial infection a therapeutically effective amount of one or more compounds of Formula (II) and/or salt(s) thereof:

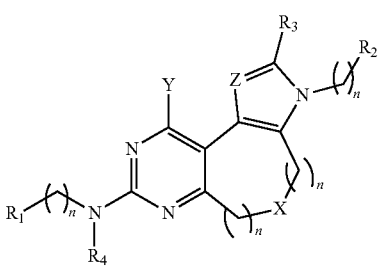

(II)

wherein $R_1$-$R_4$ are independently selected from the group consisting of hydrogen, alkyl, alkenyl, heteroalkyl, cycloalkyl, heterocycloalkyl, aryl, heteroaryl, alkyl-aryl, alkyl-heteroaryl, amide, sulfonamide, and urea, wherein the alkyl, alkenyl, heteroalkyl, cycloalkyl, heterocycloalkyl, aryl, heteroaryl, alkyl-aryl, alkyl-heteroaryl are optionally substituted with one or more substituents selected from the group consisting of $(C_1$-$C_{10})$-alkyl, $(C_1$-$C_{10})$-alkenyl, cycloalkyl, heterocycloalkyl, aryl, heteroaryl, alkoxy, amide, sulfonamide, urea, halo, hydroxy, $C(O)OR_5$, and $C(O)R_6$, wherein $R_5$ is selected from the group consisting of hydrogen, alkyl and alkenyl and $R_6$ is selected from the group consisting of hydrogen, alkyl, alkenyl, heteroalkyl, cycloalkyl, heterocycloalkyl, aryl, heteroaryl and $NR_7R_8$, wherein $R_7$ and $R_8$ are independently selected from the group consisting of hydrogen, alkyl, alkenyl, aryl and heteroaryl; and wherein X is selected from the group consisting of $CR_9R_{10}$, O, S, $SO_2$, and $NR_{11}R_{12}$, and wherein Y is selected from the group consisting of OH and $NR_{13}R_{14}$, wherein $R_9$-$R_{14}$ are independently selected from the group consisting of hydrogen, alkyl, heteroalkyl, cycloalkyl, heterocycloalkyl, alkenyl, aryl, heteroaryl, amide, sulfonamide, urea and $C(O)R_{15}$ wherein $R_{15}$ is selected from the group consisting of hydrogen, alkyl, alkenyl, heteroalkyl, cycloalkyl, heterocycloalkyl, aryl and heteroaryl and wherein $R_{13}$ and $R_{14}$ may optionally form a ring structure; and n is an integer from 0 to 5; and wherein Z is independently selected from the group consisting of C and N; and n is an integer from 0 to 5.

Figure 15:
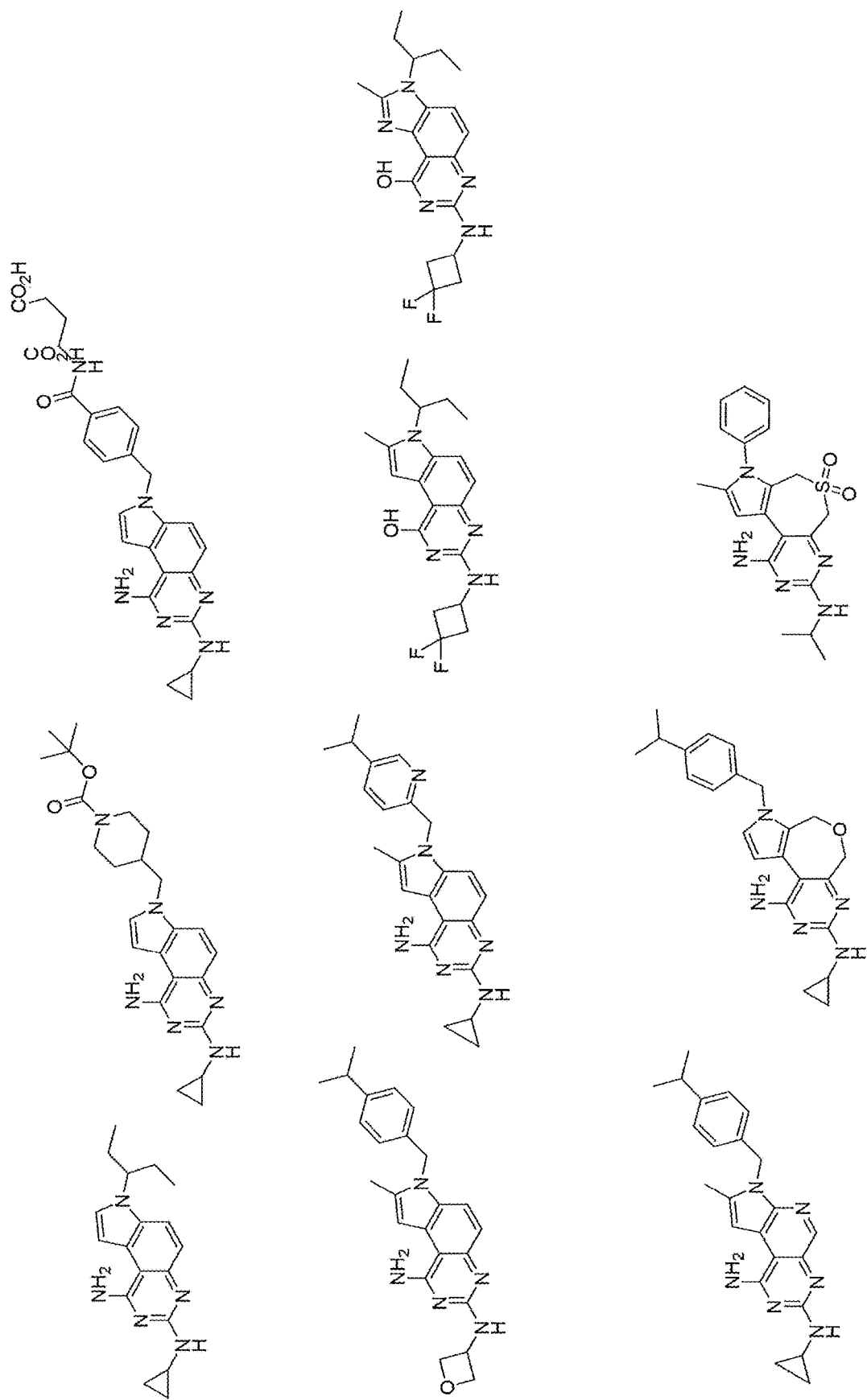
FIG. 15 and FIG. 16 illustrate various non-limiting examples of compounds of Formula (I), (IA) and Formula (II).
Figure 16:
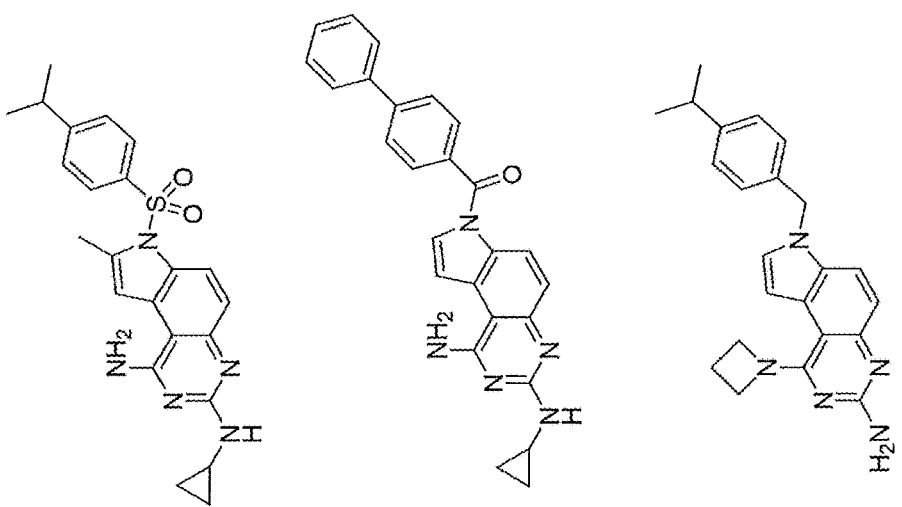
Figure 16:
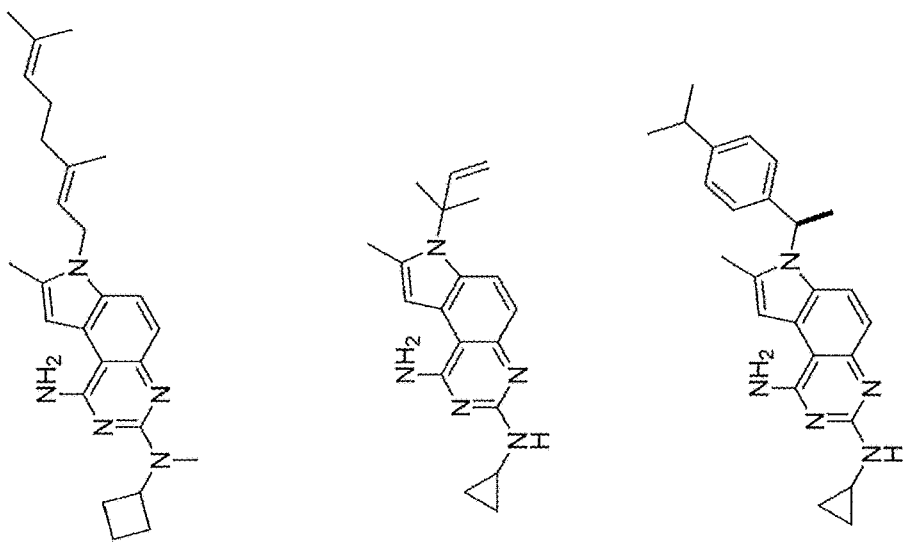
Figure 16:
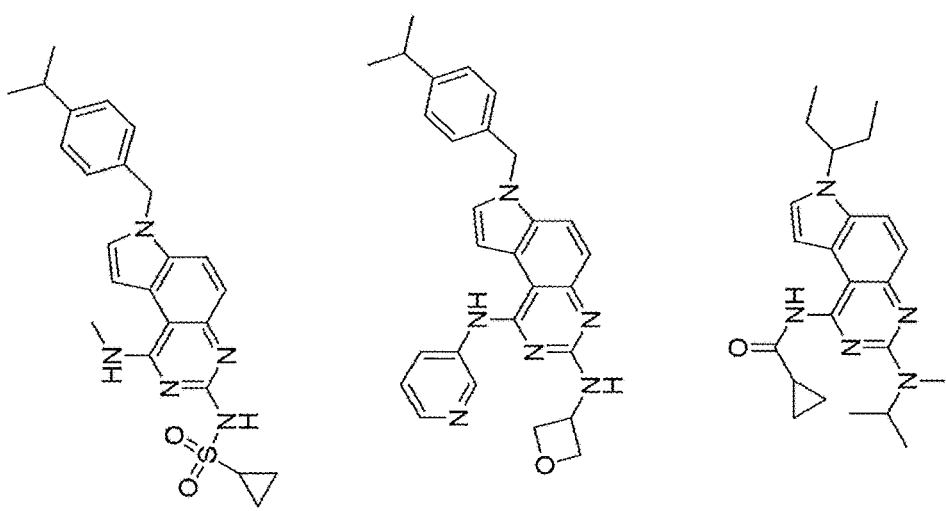
Figure 17:
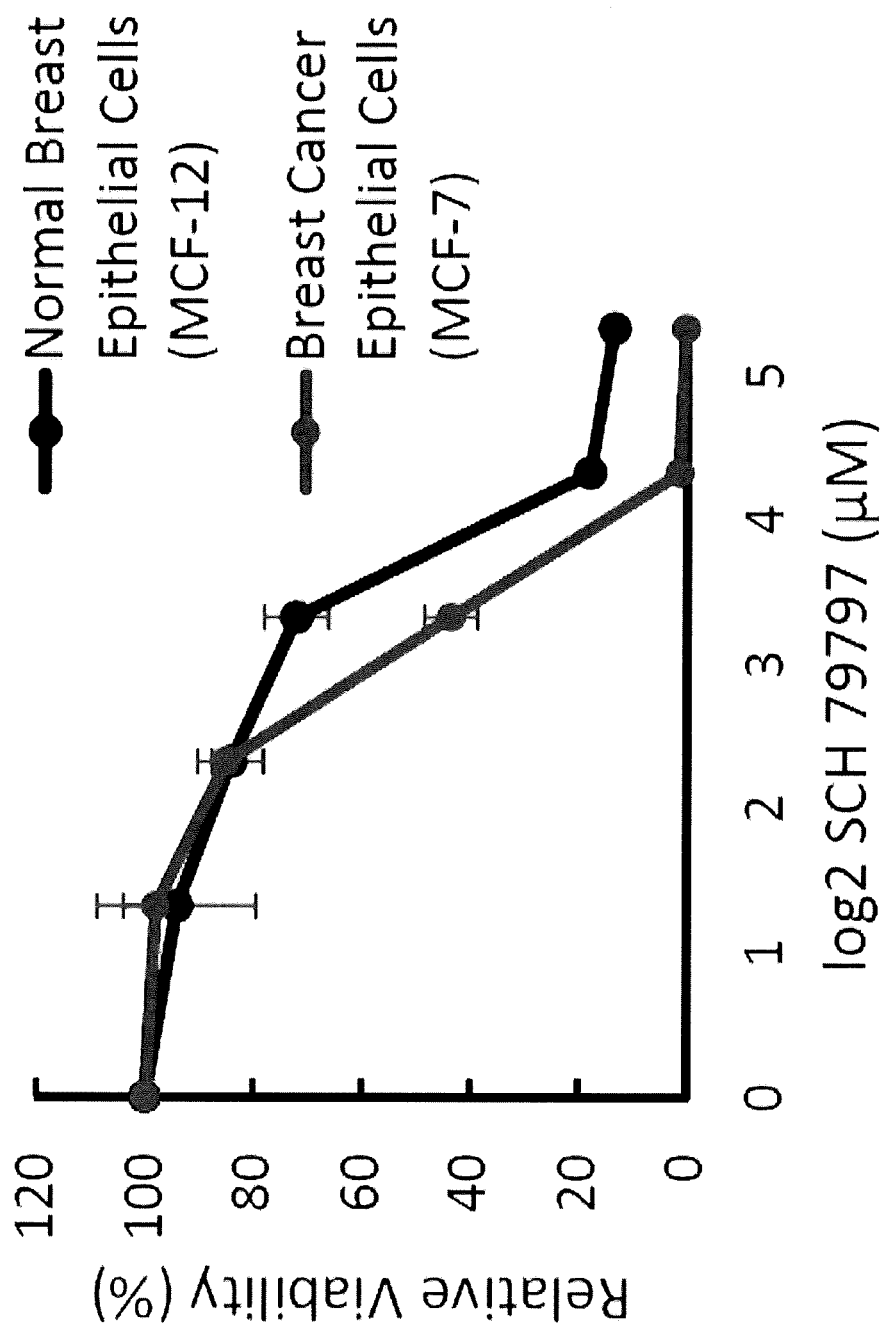
FIG. 17 illustrates anticancer activity of a compound described herein for breast cancer cells.

FIGS. 15 and 16 illustrates various non-limiting examples of compounds of Formula (I), (IA) and Formula (II). In some embodiments, bacteria of the infection treated with compounds described herein are gram positive. Alternatively, bacteria of the infection can be gram negative. Moreover, as detailed further below, compounds of Formula (I), (IA) and Formula (II) can exhibit activity against resistant and/or clinically significant pathogens including, but not limited to, MRSA, *S. aureus, N. gonorrhoeae* and several isolates and *A. baumannii*. Moreover, compounds of Formula (I), (IA) and Formula (II), in some embodiments, can exhibit more than one mode of action. For example, compounds described herein can target folate synthesis while inducing cell membrane depolarization and/or membrane permeability. By exhibiting a plurality of modes of action, compounds of Formula (I), (IA) and Formula (II) inhibit the ability of bacteria and/or other pathogens to develop resistance to these compounds.

Compounds and/or salt(s) of Formula (I), (IA) and Formula (II) can be administered in any amount consistent with treating bacterial infections. In some embodiments, one or more of the compounds are administered in an amount of 1 μg/ml to 1 mg/ml. In some embodiments, one or more of the compounds are administered in an amount of 1 μg/ml to 100 μg/ml or 1 μg/ml to 15 μg/ml. Additionally, compounds and/or salt(s) of Formula (I), (IA) and Formula (II) can be combined with any physiologically suitable carrier or excipient.

In another aspect, pharmaceutical compositions are described herein. In some embodiments, the pharmaceutical compositions are operable for treating bacterial infections and/or cancerous tissue. A pharmaceutical composition, in some embodiments, comprises a compound of Formula (I), Formula (IA) and/or Formula (II) and/or salt(s) thereof. General structures of Formula (I), Formula (IA) and Formula (II) are provided hereinabove. Moreover, several non-limiting embodiments are illustrated in FIGS. 15 and 16. The pharmaceutical compositions can comprise any amount(s) of one or more compounds of Formula (I), Formula (IA) and/or Formula (II) consistent with the pathogen being treated.

In another aspect, methods of treating bacterial infections are described herein employing compounds previously unknown to exhibit antibacterial activity.

I. Primary Screen

With the aim of finding antibiotics with novel MOAs, an unbiased whole-cell screening approach was applied. To include antibiotics that target either gram-negative and gram-positive bacteria, compounds were screened that inhibited growth of the *E. coli* MC4100 imp4213 (imp) strain, which has a compromised OM that makes it permeable to antibiotics that would otherwise not penetrate the gram-negative lipolysaccharide (LPS). 33,434 unique compounds spanning 5 libraries were screened, with 32,343 compounds represented once, 923 duplicates, 114 triplicates, 12 quadruplicates and 2 compounds represented five times, all at the concentration of 50 uM in DMSO.

To amplify the 'growth' signal compound-exposed *E. coli* imp cultures were screened in Terrific Broth, which yielded a higher maximum culture optical density. After normalizing for plate-to-plate variation, an OD600 of half the median plate OD600 was used as a generous arbitrary cutoff, below which any compound was assumed to have inhibited the growth of the imp strain and above which compounds were assumed to be ineffective (see FIG. 1). This resulted in just fewer than 190 unique hits whose structures were characterized using the extended molecular fingerprinting method and then compared using their Jaccard similarity index.

To understand where in chemical space antibacterial compounds reside in comparison to all other molecules in the library, the water to octanol partitioning coefficient was calculated employing the proven XLOGP algorithm and, for every screened molecule, these values were plotted against the molecular weight of each compound (see FIGS. 2A and 2B). This analysis confirmed that antibiotic molecules were both significantly more hydrophobic (p-value $2 \times 10^{-2}$) and more massive (p-value $9.5 \times 10^{-13}$) than the average compound in the screening collection.

II. MIC Determination of Hits

From the 186 unique hits, 32 lead compounds were selected that either had not been identified as antibiotics or had unknown or ambiguous MOAs for further investigation. To understand the potency of these compounds, their minimum inhibitory concentration (MIC) was measured on the imp strain using the microdilution method in 96-well plates. The 32 leads were pared down to the 20 most potent plus the single remaining Chiromics library compound that still displayed activity. These compounds and their MICs are provided in Table I.

TABLE I

Lead Compound MICs

| Compound | MIC (μM) |
|---|---|
| Rivaroxaban | 0.05 |
| Bleomycin | 0.1 |
| AZT* | 0.2 |
| Calmidazolium chloride | 3.125 |
| ONO-RS-082 | 3.125 |
| AZT* | 3.125 |
| Tramadol hydrochloride | 6.25 |
| AC-93253 iodide | 6.25 |
| Floxuridine | 6.25 |
| Auranofin | 6.25 |
| GW5074 | 6.25 |
| Dichlorophen | 12.5 |
| DL-erythro-dihydrosphingosine | 12.5 |
| Alexidine hydrochloride | 12.5 |
| H 89 dihydrochloride | 12.5 |
| Homidium bromide | 25 |
| Bronopol | 25 |
| Idarubicin | 25 |
| Triflupromazine | 25 |
| SCH 79797 | 25 |
| Chlormidazole | 25 |
| CP000294 | 125 |

*A span of AZT concentrations that inhibited growth of cells with an intervening region of growth was observed.

III. High-Throughput Bacterial Cytological Profiling

To determine the MOAs of the lead compounds, a single-cell, high-content imaging methodology known as bacterial cytological profiling, BCP, was improved upon. First, a training set of compounds with known MOAs spanning 37 distinct antibiotic drug families was assembled for comparison to the present set of unknown leads. Other than increasing the throughput of the BCP assay by making 45 agarose pads per slide which gives the method a throughput of approximately 100 samples a day, the exact same set of dyes, relative antibiotic concentrations, and cell preparatory methods were used as previously described in Poochit Nonejuie et al., Bacterial cytological profiling rapidly identifies the cellular pathways targeted by antibacterial molecules, *Proceedings of the National Academy of Sciences of the United States of America* 110.40 (October 2013), pp. 16169-16174. Additionally, since it was sought to assay the 21 lead compounds simultaneously, it was neglected to divide and compare each lead within inhibitor subclasses. Instead, the data was simply imaged and analyzed as a single aggregate.

In total, 14 features were extracted from each single antibiotic treated cell, which were divided into three classes. The cell morphology class consisted of measurements of area, length, width and eccentricity. For the nucleoid morphology class, these same features were measured, but of the nucleoid, plus an additional feature which is the ratio of nucleoid area to cell area, termed nucleoid decondensation. Finally, the mean intensity of each of the dyes, Sytox Green, Dapi and FM4-64, for the membrane permeability class were measured. These data were then compared using three complimentary approaches: a simple principle component analysis (PCA) on the means of each feature for each antibiotic treatment group, a PCA on the means with an additional set of group features composing the variance of each feature for each antibiotic treatment class, and finally a neighborhood defining method that makes pairwise comparisons of the mahalanobis distances of each group to all other groups. The first method neglected the variance in cell death while the final two attempted to account for it.

To make each feature comparable for the dimensional reduction analyses, each feature was log 2-scaled and subsequently mean-centered and scaled by its variance. In both of these analyses it was decided to keep principle components until greater than 90% of the cumulative variance was accounted for. In the simple average feature scheme, this resulted in reducing the number of dimensions down to 4 from the original 14. For the second scheme where the averages and the variances were employed, which were also mean-centered, of each feature as dimension this requirement reduced the dimensions down to 6 from 28. The loadings for each of the principle components that were kept are shown in FIG. 3 for the simple averages and FIG. 4 for the averages paired with their variances.

Figure 5:
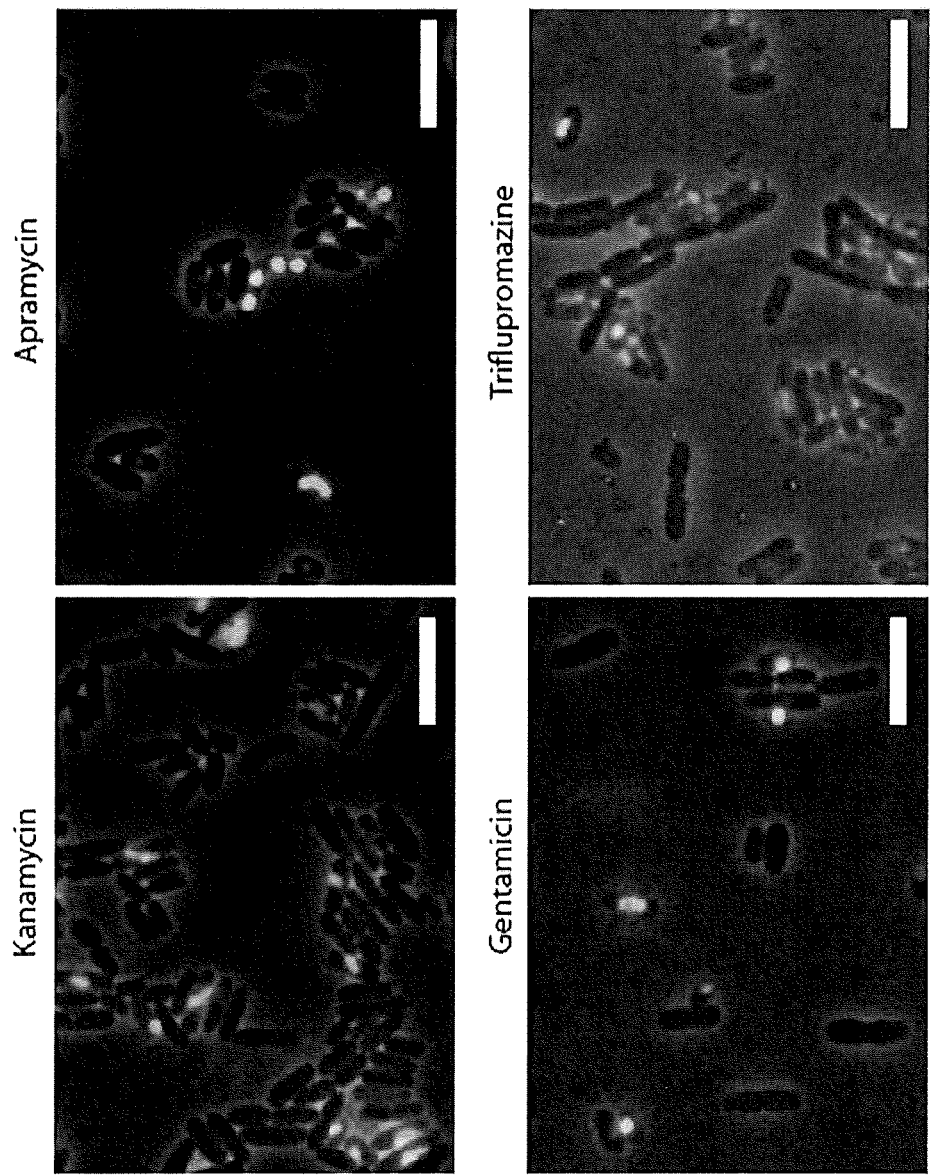
FIG. 5 illustrates bacterial cytological profiles of 4 antibiotics from the same neighborhood; Kanamycin, Apramycin and Gentamicin are well-known aminoglycosides while the MOA of triflupromazine is unknown; Merged image channels are phase (grey), FM4-64 (red), Sytox (green) and Dapi (blue); scale bar is 5 µm.

The final data analysis scheme took the heterogeneity observed in the antibiotic-treated cell groups into account without reducing the dimensions of the data, while also accounting for position of a single treatment group in the context of all other groups. For each treatment group, a neighborhood representation vector was populated with the one-way mahalanobis distance as measured from the single-cell feature mean in question to the distributions measurement of all other treatment groups. This distance was normalized by the covariance matrix of the antibiotic treatment group so that dimensions with large amounts of variance, for example in the case of triflupromazine mean Sytox stain intensity per cell (see FIG. 5), were deemed closer while distances of dimensions with less variance are considered farther away. Treatment groups were then single-linkage clustered by their neighborhood representation vectors, such that samples whose neighborhoods were similar would be clustered together.

IV. Triflupromazine and Aminoglycoside Antibiotics Both Activate the cpx Envelope Stress Response in *E. coli*

Cytological profiling has been heralded as being capable of accurately pairing, not just the MOAs of antibiotics that inhibit the same pathway, but even differentiating between different molecular targets on the same molecule. It was sought to understand how closely families of cell-death states, as reported by the neighborhood analysis described herein, were in their overall response to the antibiotics in question. To this end, the clustered family consisting of three well-known aminoglycosides (kanamycin, apramycin, and gentimicin) was selected along with an antipsychotic that was observed to bear antibacterial activity(triflupromazine) but whose MOA was in question.

Figure 6:
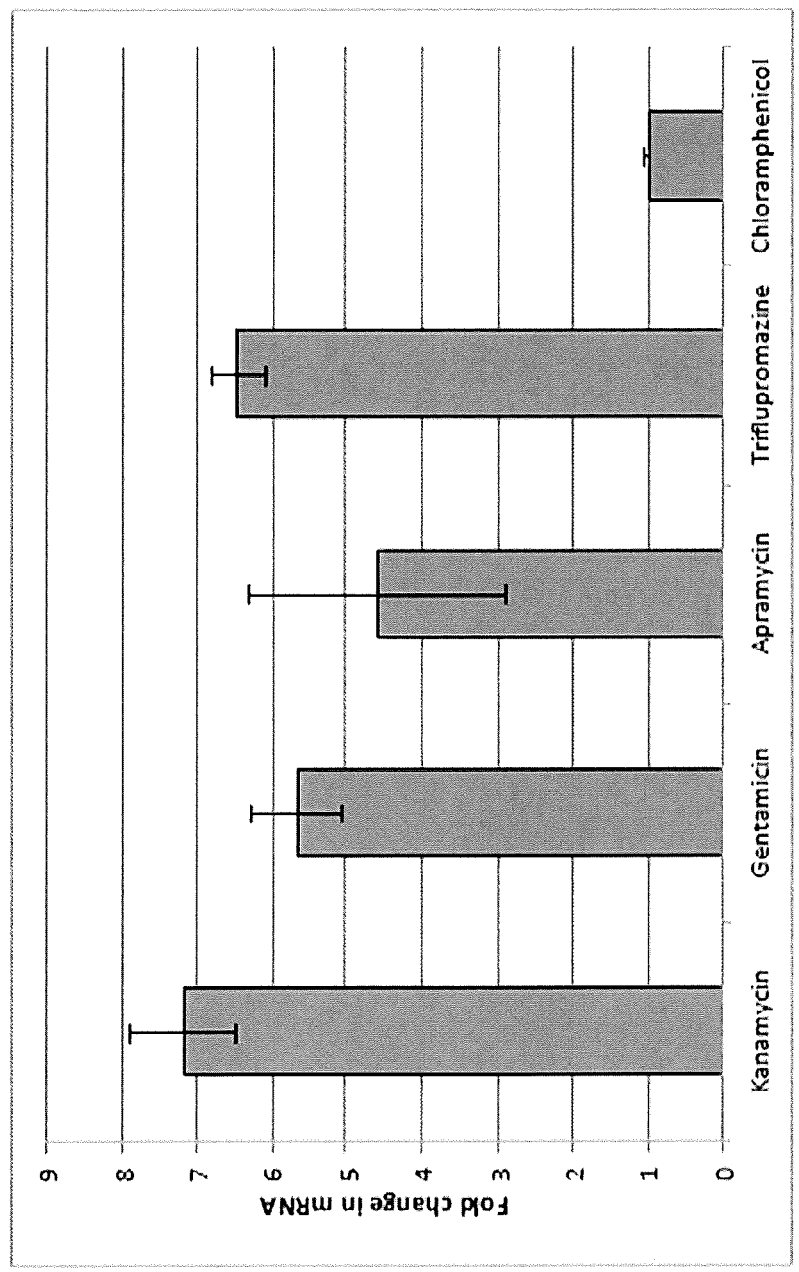
FIG. 6 illustrates cell envelope stress response activation by mistranslation-causing AGAs and triflupromazine; mRNA levels are normalized to the mRNA of the unperturbed ubiJ gene for each experiment; error bars represent S.E.M.
Figure 7A:
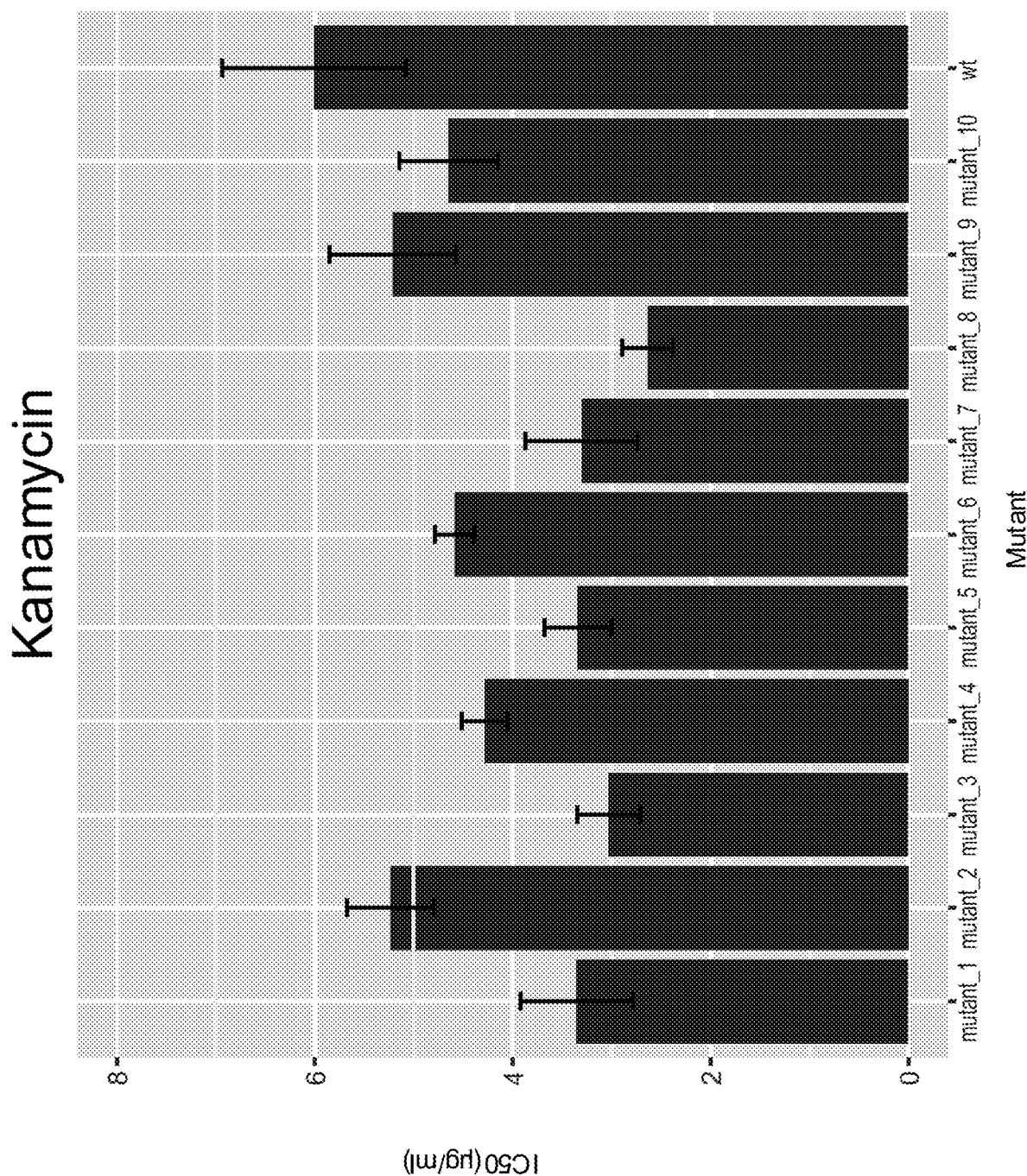
FIGS. 7(A) through 7(D) illustrate $IC50_s$ of triflupromazine resistant mutants against kanamycin, gentamicin, chloramphenicol, and triflupromazine respectively; error bars represent S.E.M.
Figure 7B:
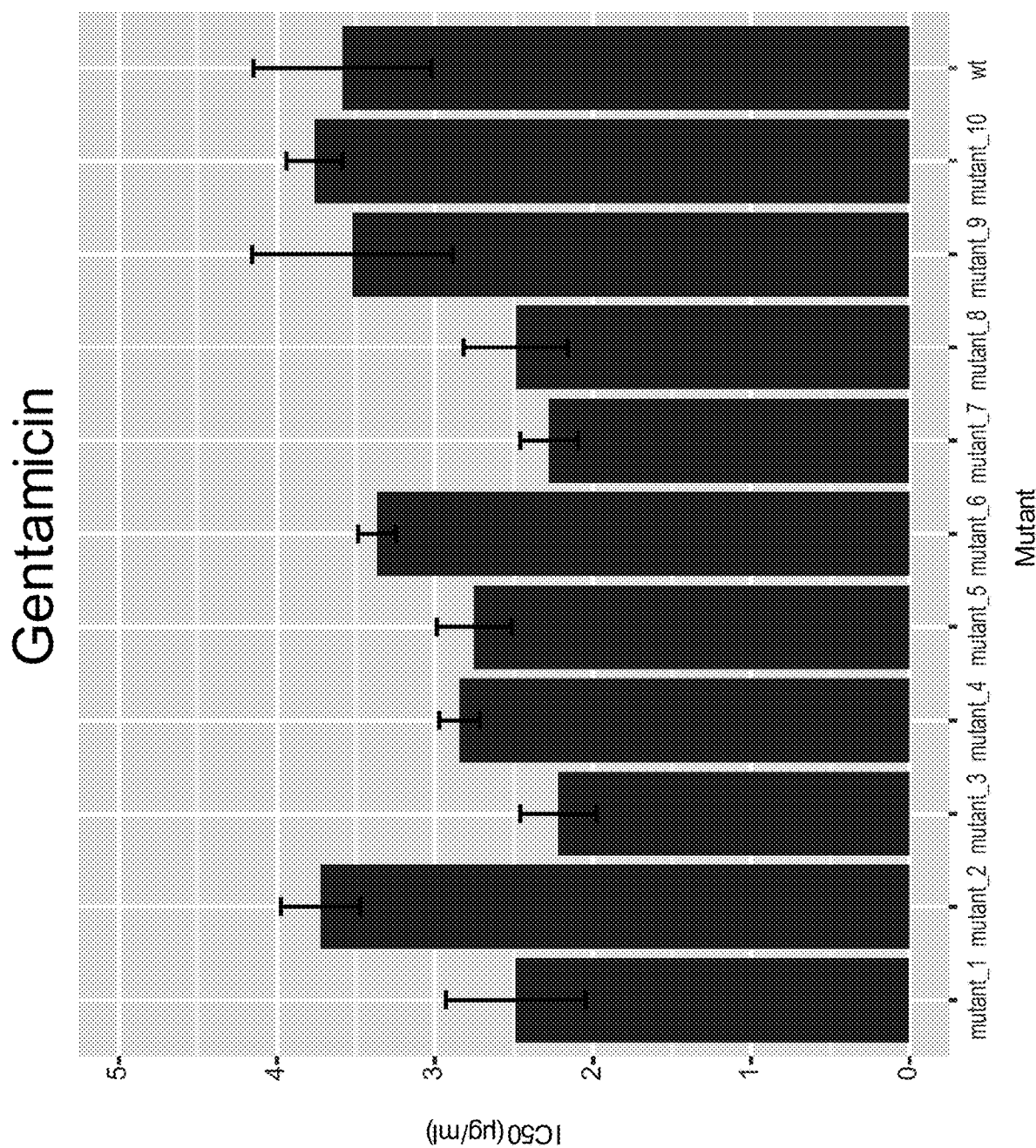
Figure 7C:
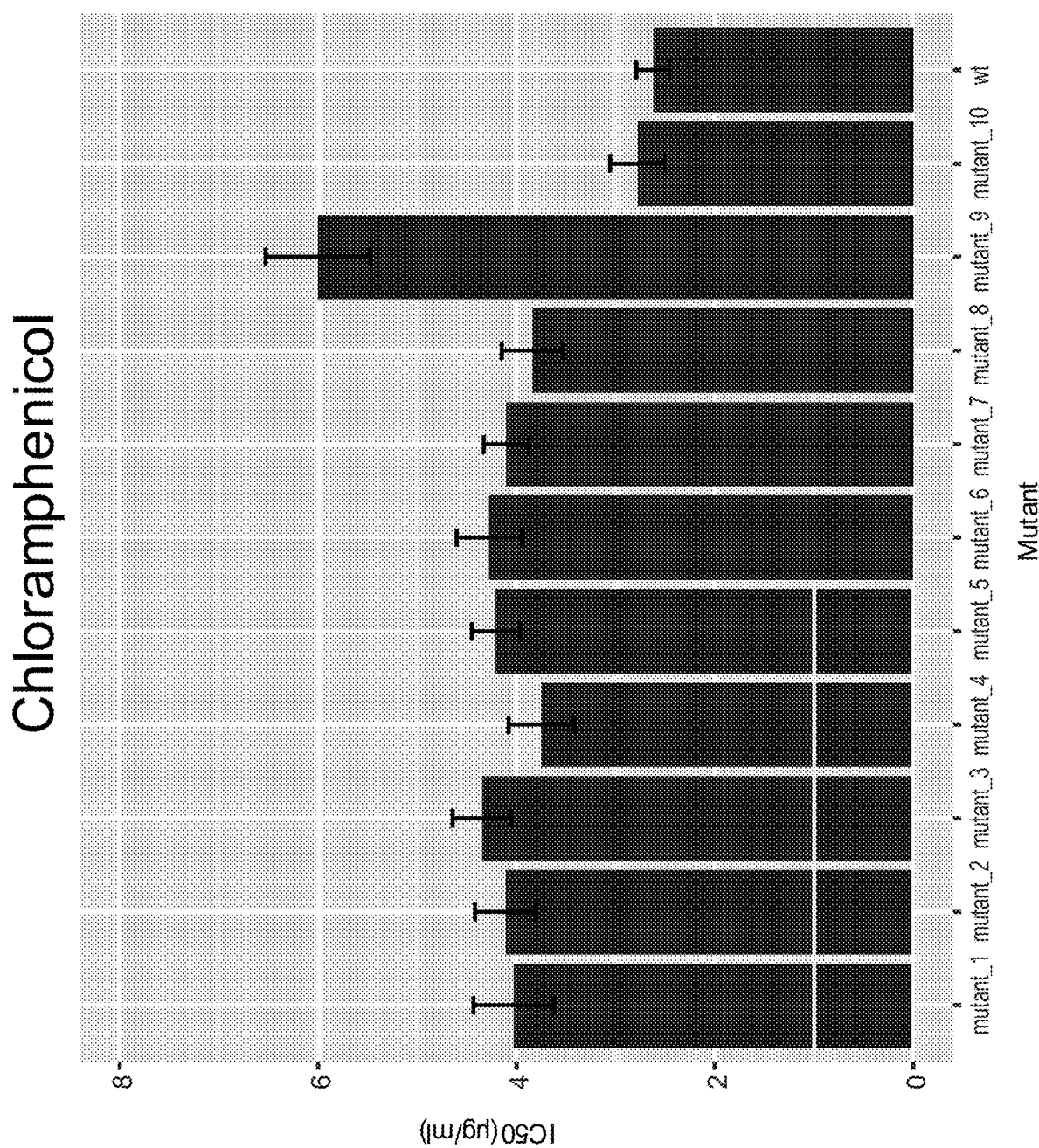
Figure 7D:
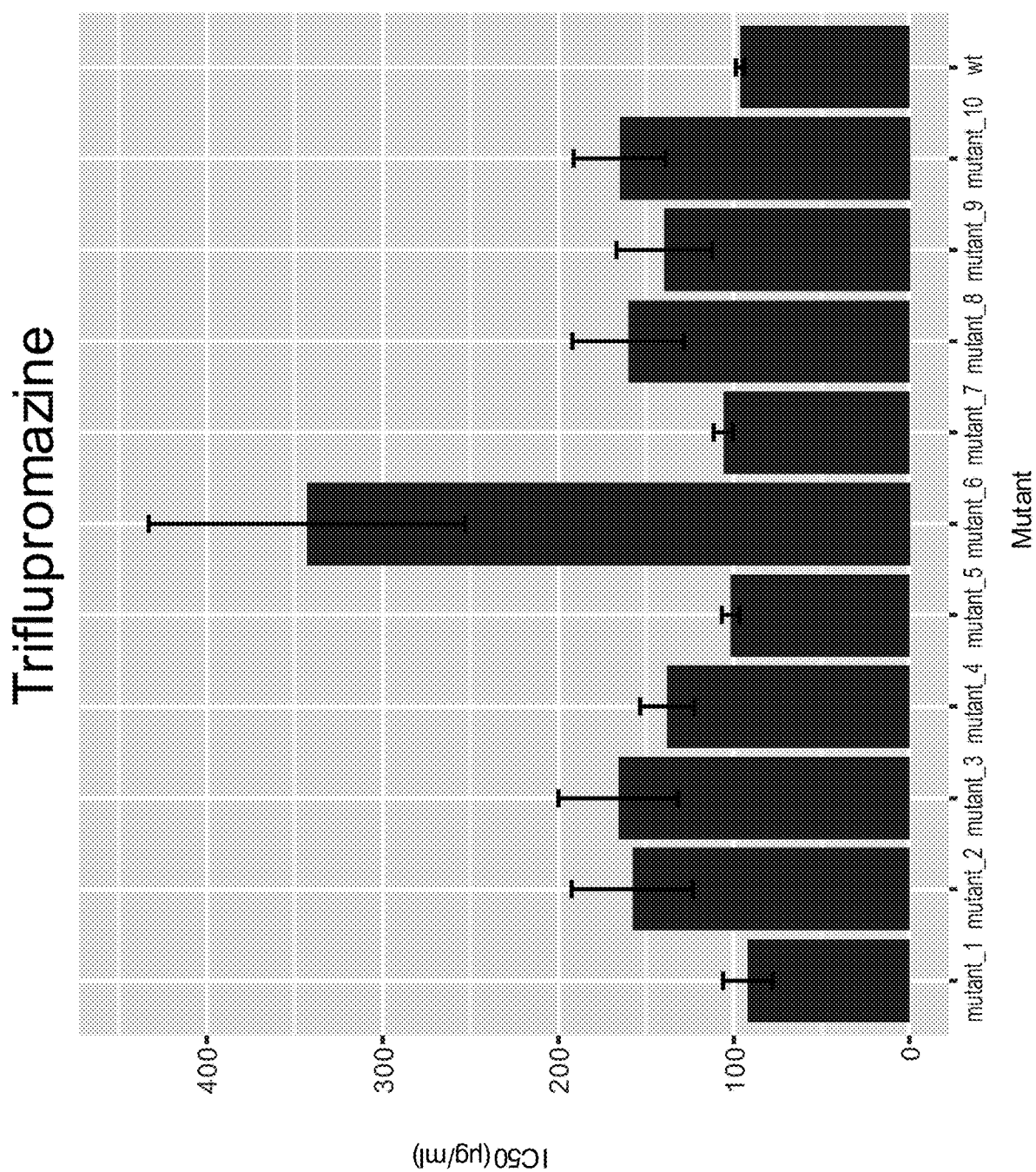

It has been suggested that aminoglycoside antibiotics (AGAs) lead to bacterial cell death by inducing mistranslation of cytoplasmic membrane-associated proteins which compromise the lipid bilayer. Thus, that the three AGAs fell into a distinct neighborhood not similar to the other ribosome-targeting antibiotics was unsurprising. Since the Cpx envelope stress response has been implicated in conferring AGA resistance to *E. coli* it was decided to measure its transcriptional output, by proxy of activation of the negative regulator cpxP which has been shown to be induced upon envelope stress. Using drug concentrations that were within one to one-half the MIC, which for the AGAs and chloramphenicol was 5 µg/ml and for triflupromazine was 50 µg/ml, it was found that in *E. coli* MC4100 wild type cells kanamycin, apramycin, gentamicin and triflupromazine all induced cpxP expression while the non-AGA ribosomal targeting drug chloramphenicol did not (see FIG. 6).

V. Triflupromazine Resistance Does Not Confer Resistance to AGAs

Having confirmed that triupormazine and AGAs induce the same stress response, it was sought to see if they might bind to the same molecular targets. To do this, *E. coli* was selected that could form colonies on plates with 400 µg/ml triflupromazine, 4 times the MIC in liquid LB media. 10 mutants were chosen that conferred heritable resistance to triflupromazine and measured their IC50s against triflupromazine, kanamycin, gentamicin, and chloramphenicol. While all 10 mutants either had similar or elevated resistance to triflupromazine, none gained increased resistance to the AGAs (see FIG. 7). Interestingly, 9 out of the 10 mutants gained increased resistance to chloramphenicol, as measured by the IC50.

VI. Compounds with Novel MOAs have Broad-Spectrum Activity

Figure 8:
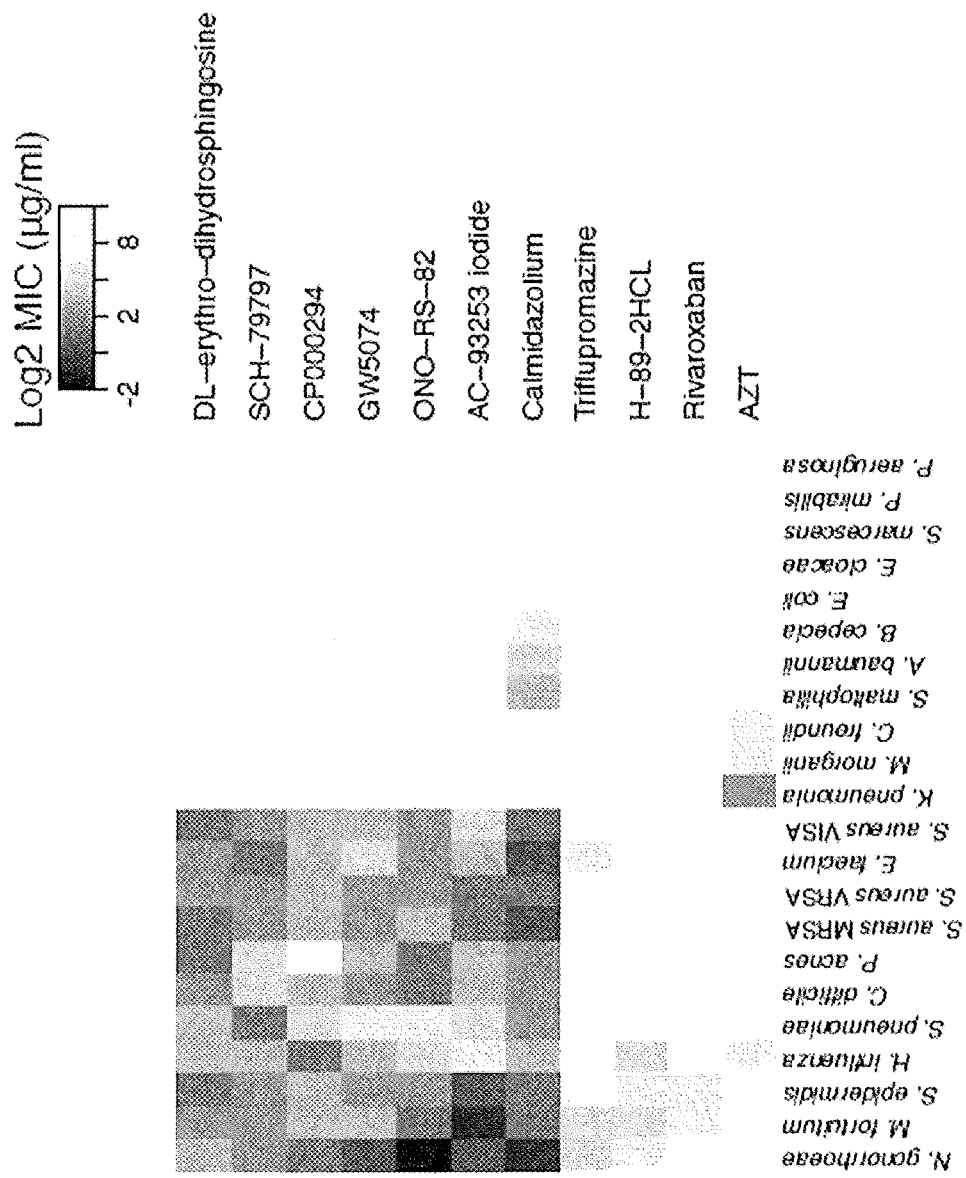
FIG. 8 illustrates bacterial cytological profiles of antibiotics with potentially novel MOAs.
Figure 9:
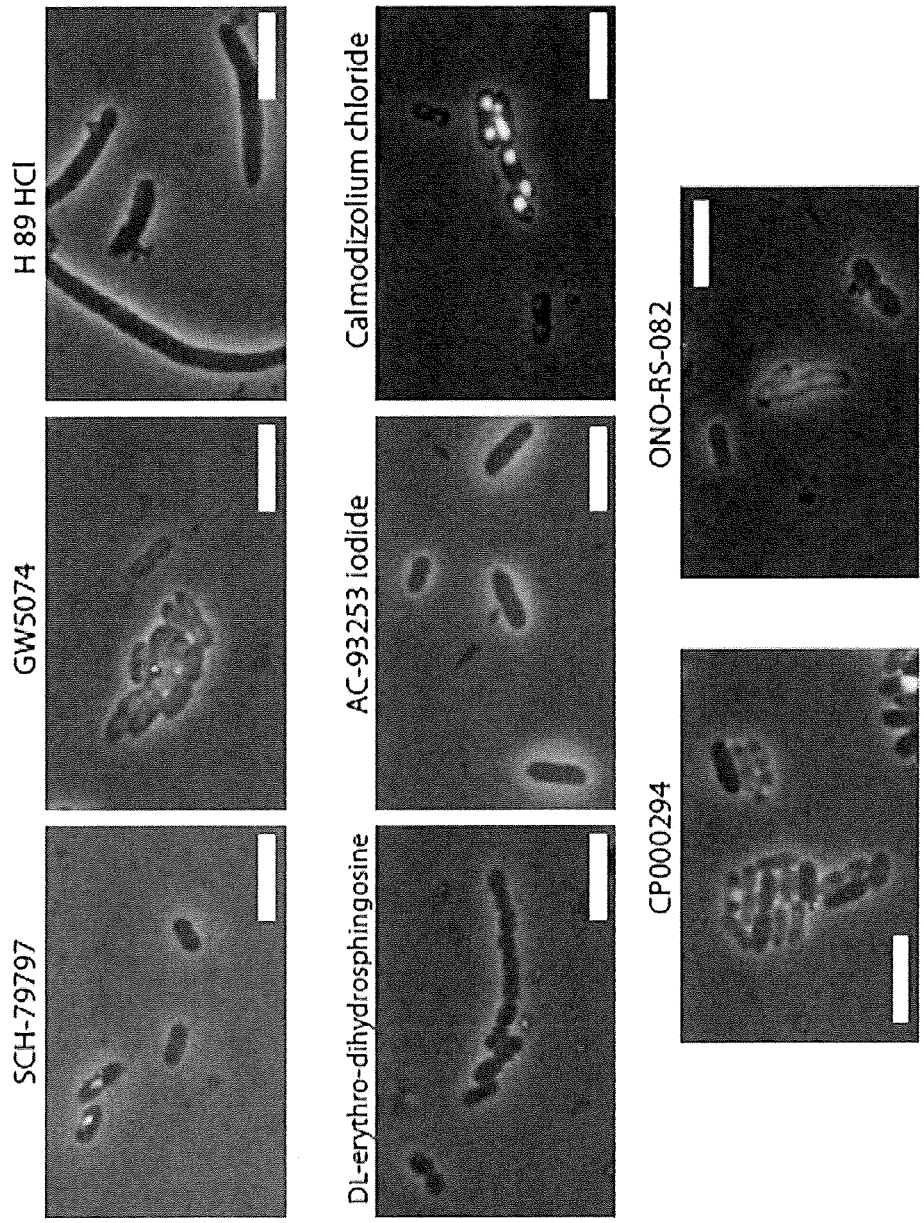
FIG. 9 illustrates MICs of unknown antibiotics against clinically important pathogens according to some embodiments; merged image channels are phase (grey), FM4-64 (red), Sytox (green) and Dapi (blue); scale bar is 5 µm.

The mahalanobis distance based analysis suggests that 8 of the 21 lead compounds cause phenotypic death-states unlike any other of the antibiotics tested (see FIG. 9). In an effort to understand how effective these 8, possibly novel, antibiotics might be in treating infections, their MICs against a panel of 22 clinically important pathogens shown in Table II were measured. In addition, the MICs of 3 other compounds of interest, rivaroxaban, AZT, and triflupromazine, were measured which were associated with specific drug classes. The results of these MIC spectrum screens are shown in FIG. 8. Of particular interest, ONO-RS-82 inhibited *C. difficile* and *N. gonorrhoeae* with at concentrations of 2 µg/ml and 0.25 µg/ml respectively. Calmodizolium chloride also inhibited *E. faecium*, *N. gonorrhoeae* and methicillin resistant *S. aureus* at concentrations all less than 1 µg/ml.

TABLE II

Strains used in MIC determination of lead compounds with novel MOAs

| Species | Strain | Description |
| --- | --- | --- |
| *Clostridium difficile* | ATCC BAA-1875 | Toxigenic |
| *Propionibacterium acnes* | ATCC29399 | Human skin isolate |

TABLE II-continued

Strains used in MIC determination of lead compounds with novel MOAs

| Species | Strain | Description |
|---|---|---|
| Acinetobacter baumannii | ATCC BAA- 1710 | Multi-drug resistant |
| Burkholderia cepacia | ATCC 25416 | |
| Citrobacter freundii | ATCC8090 | |
| Escherichia coli | NCTC 13461 | CTX-M betalactamase positive |
| Haemophilus influenzae | ATCC35056 | |
| Klebsiella pneumoniae | ATCCBAA-1705 | KPC carbapenemase positive |
| Morganella morganii | ATCC25830 | |
| Neisseria gonorrhoeae | CCUG57598 | Cip-R, Cef-R |
| Proteus mirabilis | ATCC29906 | |
| Pseudomonas aeruginosa | BCCM 27650 | Multi-drug resistant |
| Serratia marcescens | ATCC13880 | |
| Stenotrophomonas maltophila | ATCC 13637 | |
| Enterobacter cloacae | ATCC BAA-1143 | ESBL |
| Enterococcus faecium | ATCC BAA-2320 | Vancomycin resistant |
| Mycobacterium fortuitum | ATCC 110 | |
| Staphylococcus aureus | NARSA NRS384 | Methicillin resistant |
| Staphylococcus aureus | NARSA VRS11b | Vancomycin resistant |
| Staphylococcus aureus | NARSA NRS17 | Intermediate vancomycin resistance |
| Staphylococcus epidermidis | ATCC 51625 | Methicillin resistant |
| Streptococcus pneumoniae | NTU HospitalTM532 | Multi-drug resistant |

In some embodiments, compounds described herein may exhibit antibacterial activity via disruption of one or more bacterial metabolic pathways. For example, one or more compounds may interfere with or disrupt the folate biosynthetic pathway. Notably, N3-Cyclopropyl-7-[[4-(1-methylethyl)phenyl]methyl]-7H-pyrrolo [3,2-F]quinazoline-1,3-diamine dihydrochloride (SCH 79797) displayed the ability to inhibit or otherwise disrupt the folate biosynthetic pathway, rending this compound effective against gram-negative and gram-positive bacteria without being prone to resistance. Details of folate metabolism disruption and antibacterial efficacy of SCH 79797 is provided in Example 1.

Example 1

Antibacterial Activity of SCH 79797

Figure 10A:
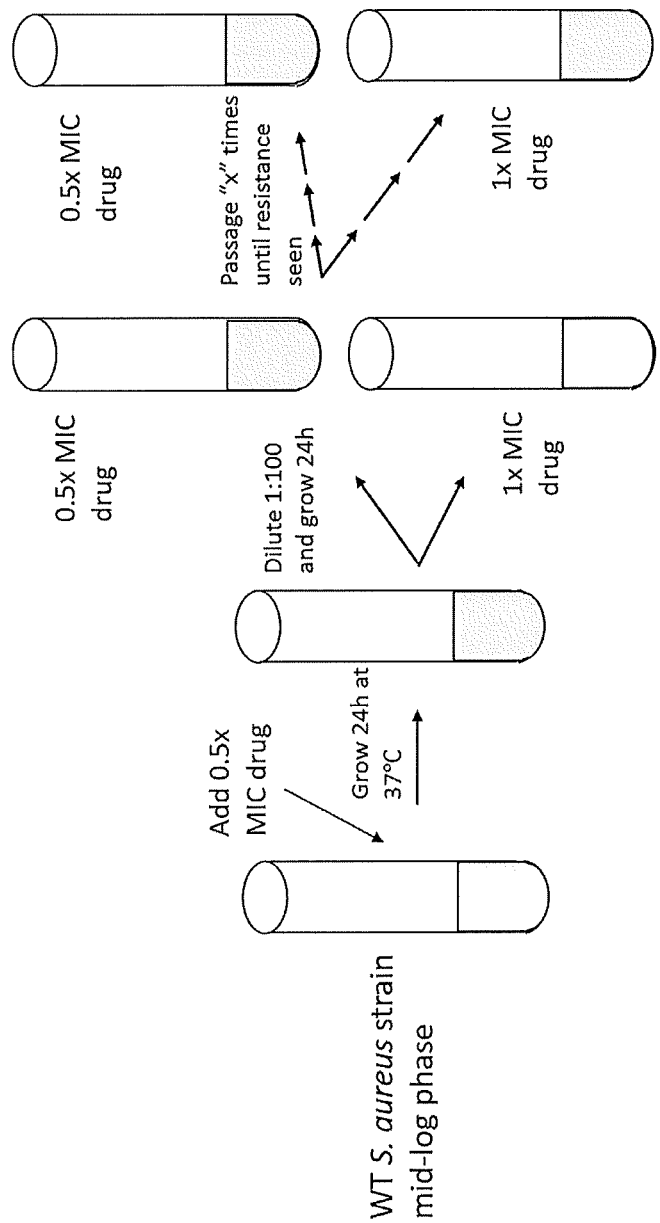
FIG. 10(A) illustrates a parental lab strain of S. aureus (HG003) was treated with a sub-lethal dose (0.5x MIC) of SCH79797, Ampicillin, and Trimethoprim and grown for 24h in TSB at 37° C. This culture was then sub-cultured into sub-lethal and lethal doses of antibiotic until growth in normally lethal doses of antibiotic was observed.

To acquire bacterial mutants that were resistant to SCH79797, a culture of WT S. aureus, HG003, was grown to mid-log phase and treated with 0.5× MIC of SCH79797, Ampicillin and Trimethoprim (FIG. 10A), After overnight growth, each treated culture was then diluted 1:100 into fresh media with either 0.5× MIC or 1× MIC of each antibiotic and grown overnight. After overnight growth, the 0.5× MIC culture of each condition was diluted 1:100 into fresh media with either 0.5× MIC or 1× MIC of each antibiotic and grown overnight. This procedure was repeated until the growth of the bacteria in 1× MIC of antibiotic was observed (FIG. 10B). As provided in FIG. 10B, bacterial resistance to SCH 79797 failed to develop.

Example 2

SCH79797 Mechanism of Action (MOA)

Figure 11A:
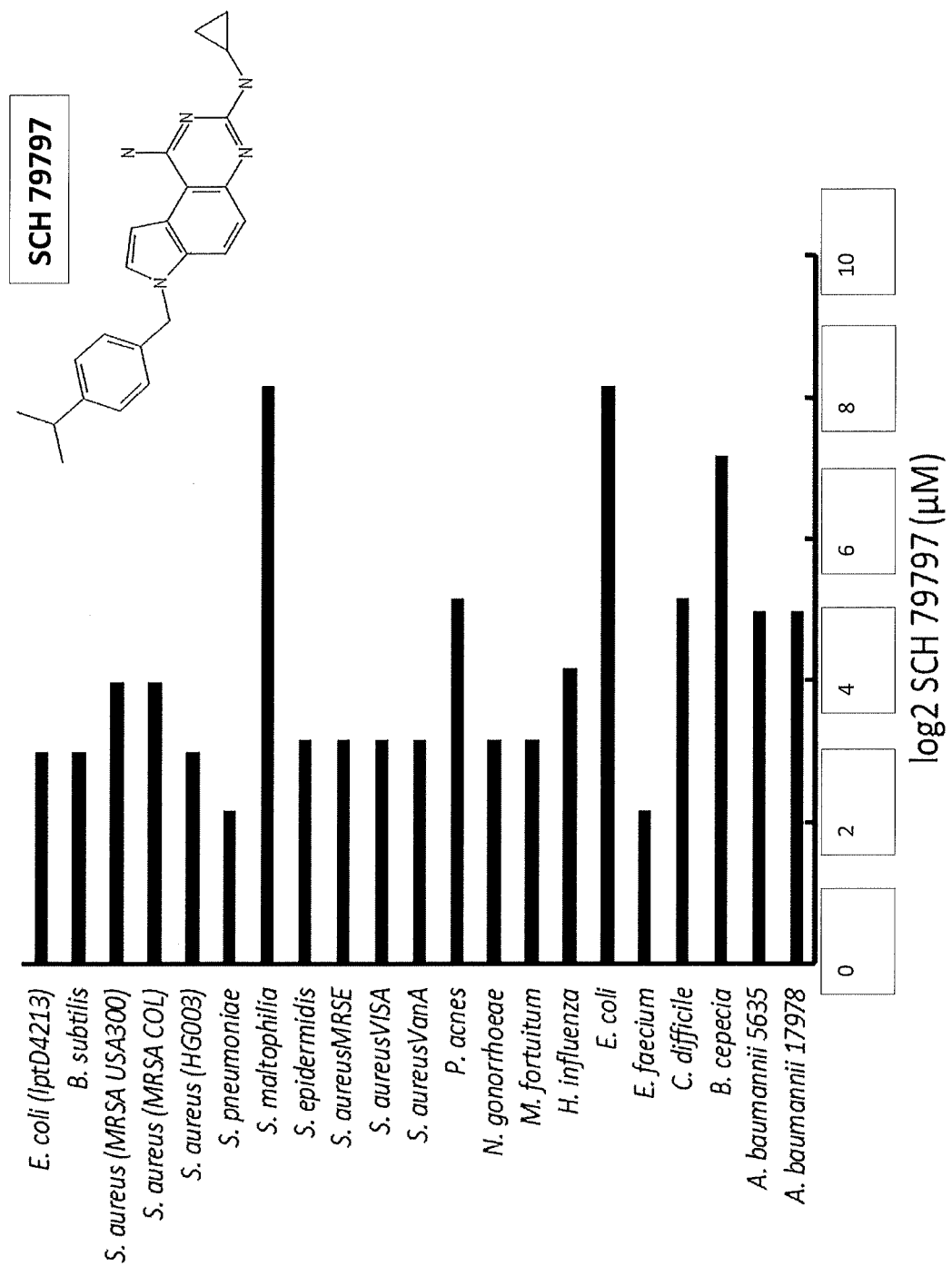
FIG. 11(A) illustrates activity of SCH 79797 against gram positive and gram negative organisms.
Figure 11B:
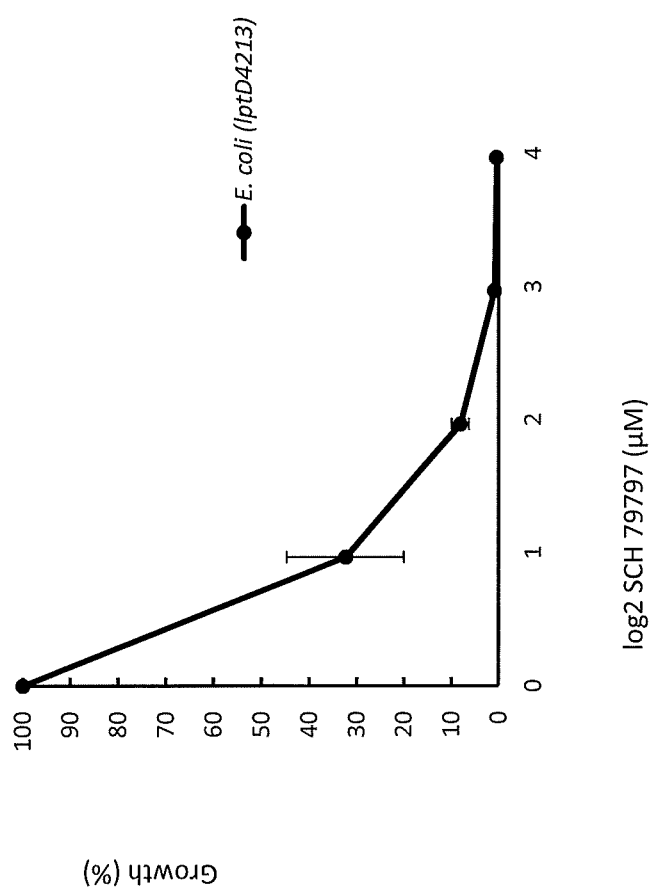
FIG. 11(B) illustrates response of E. coli (lptD4213) to SCH 79797.
Figure 11C:
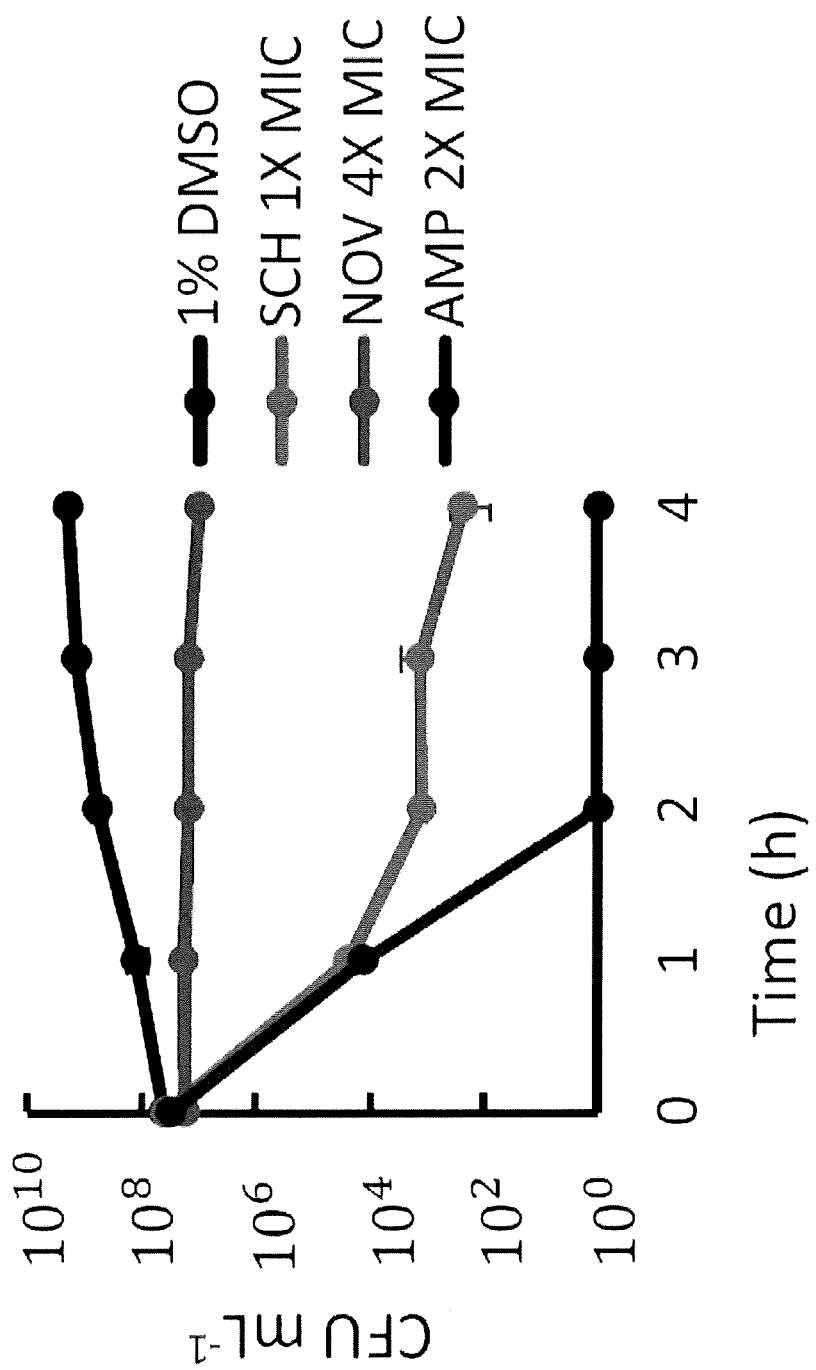
FIG. 11(C) illustrates antimicrobial activity of SCH 79797 and several other compounds.

The MOA investigation was initiated by measuring the activity of SCH 79797 (SCH) against a broad-spectrum of both gram positive and negative organisms (FIG. 11A). It was found that SCH prevented the growth of both gram positive and negative bacteria, most notably, clinically important pathogens such as MRSA S. aureus, N. gonorrhoeae and several isolates, A. baumannii. Interestingly, SCH does not have a known target in bacteria. A sensitized strain of E. coli that has a mutation in the outer membrane protein, LptD (lptD4213) was used to elucidate the mechanism of SCH (FIG. 11B). Using this strain, it was found that SCH exhibits potent bactericidal activity as illustrated in FIG. 11C.

Figure 12A:
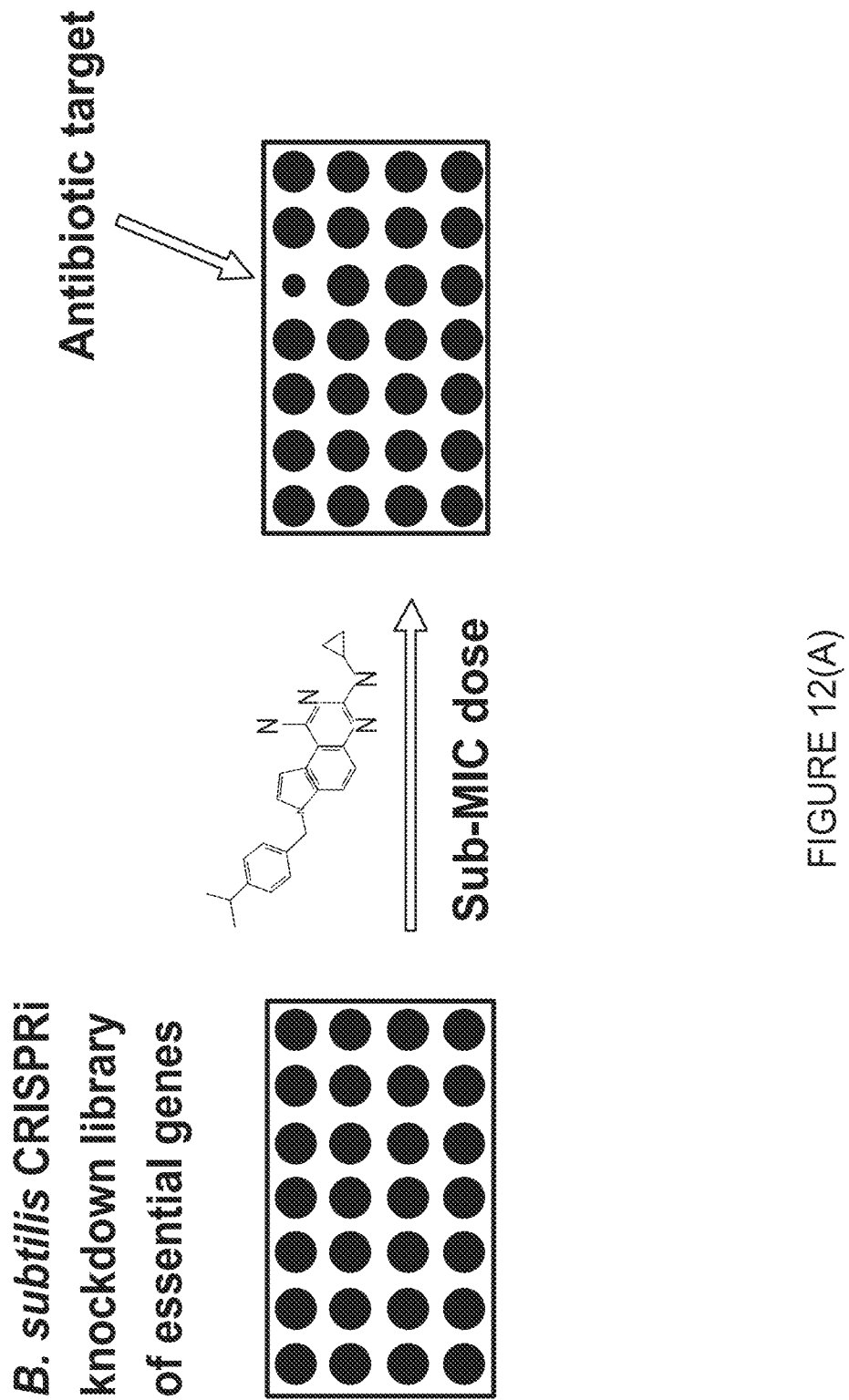
FIG. 12(A) illustrates screening of B. subtilis essential knockdown library for selection of strains sensitized to SCH.
Figure 12B:
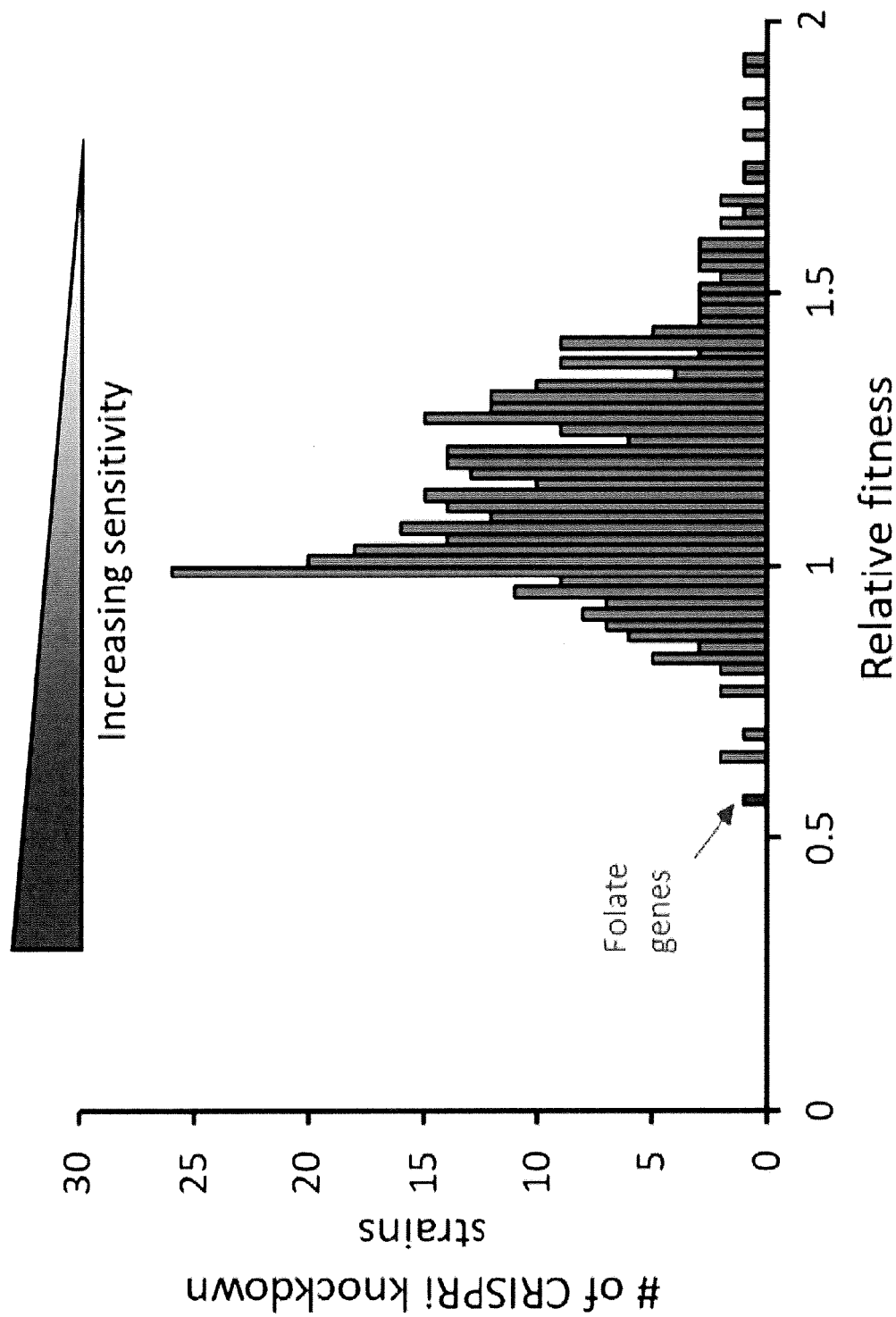
FIG. 12(B) illustrates results of the knockdown library screening.
Figure 12C:
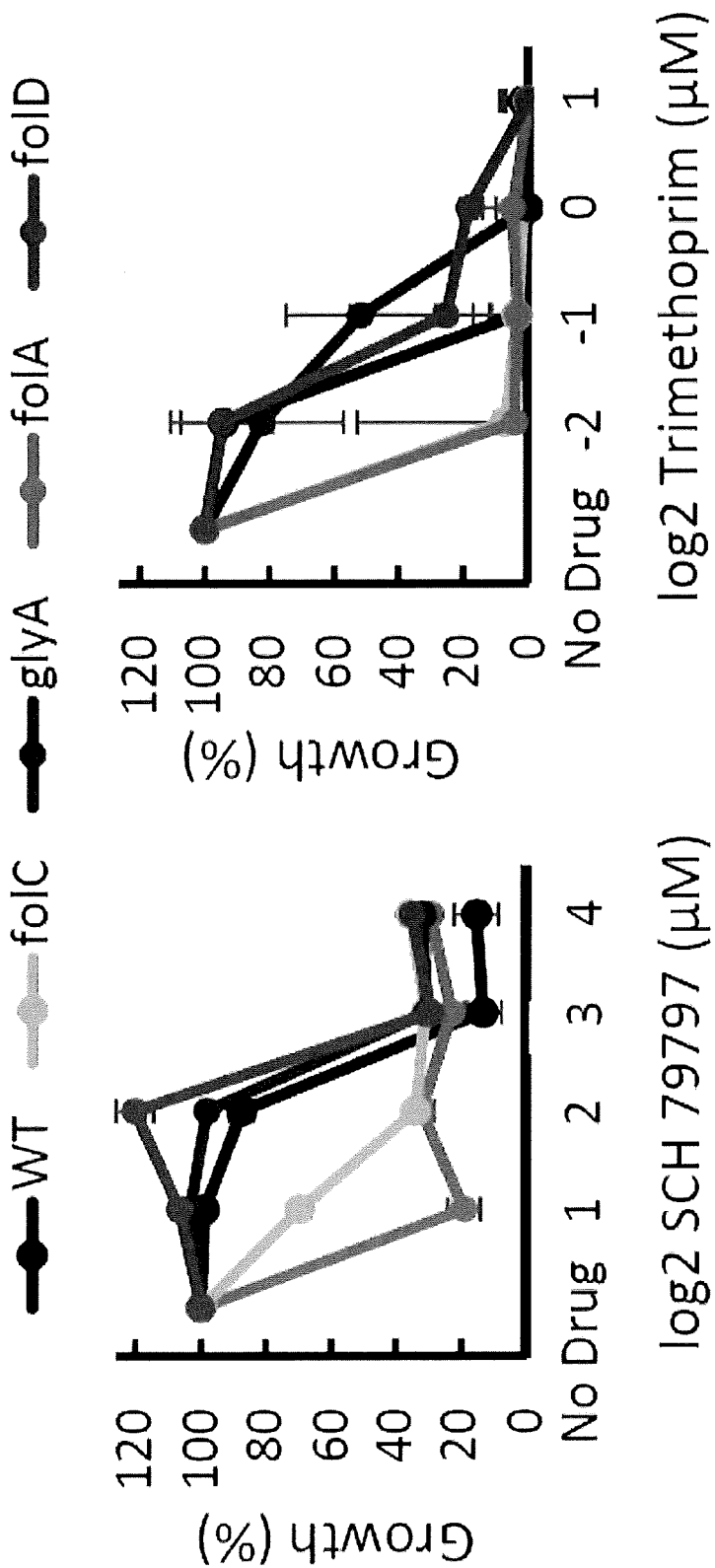
FIG. 12(C) illustrates the sensitivity of dihydrofolate reductase (folA) to SCH 79797.

The classical method of identifying the molecular target of an antibiotic is by selecting for antibiotic resistant mutants. However, SCH resistant mutants were not easily identified. A potential reason for this may be that SCH has multiple targets. To probe this hypothesis, a B. subtilis essential gene knockdown library was screened to select for strains that were sensitized to SCH (FIG. 12A). This library consists of ~300 individual strains where the expression of each essential gene is repressed 3-fold by CRISPR interference (CRISPRi). This library was pinned onto agar plates containing a sub-MIC dose of SCH and the relative fitness of each gene was measured (FIG. 12A). The dihydrofolate synthetase (folC) knockdown was the most sensitized to SCH and we confirmed its sensitivity in liquid (FIG. 12B-C). It was also found that among the essential members of the folate synthesis pathway, dihydrofolate reductase (folA), was also shown to be sensitive to SCH (FIG. 12C). Trimethoprim is a frequently used antibiotic that targets FolA. Therefore, as a control, we performed a similar analysis on the library with a sub-lethal concentration of Trimethoprim and found that both folC and folA were sensitized to Trimethoprim (FIG. 12C).

Figure 13A:
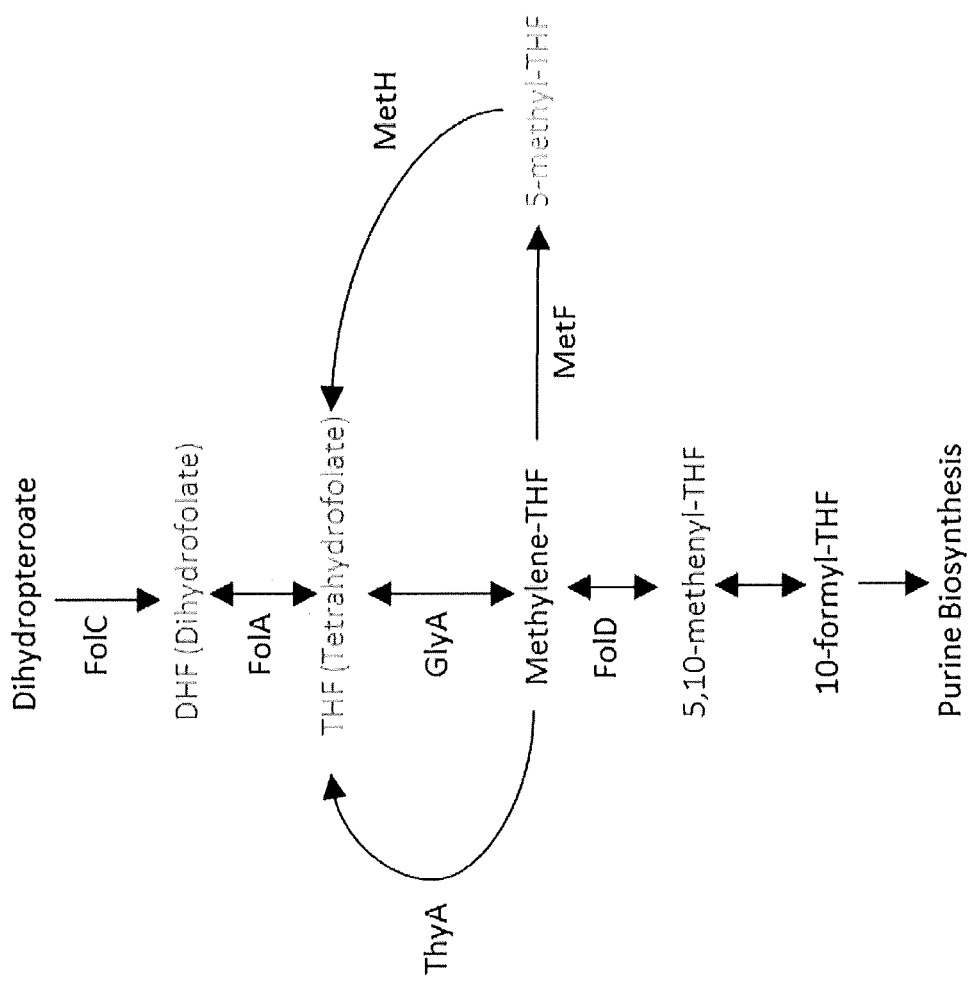
FIG. 13(A) illustrates the folate metabolic pathway.
Figure 13B:
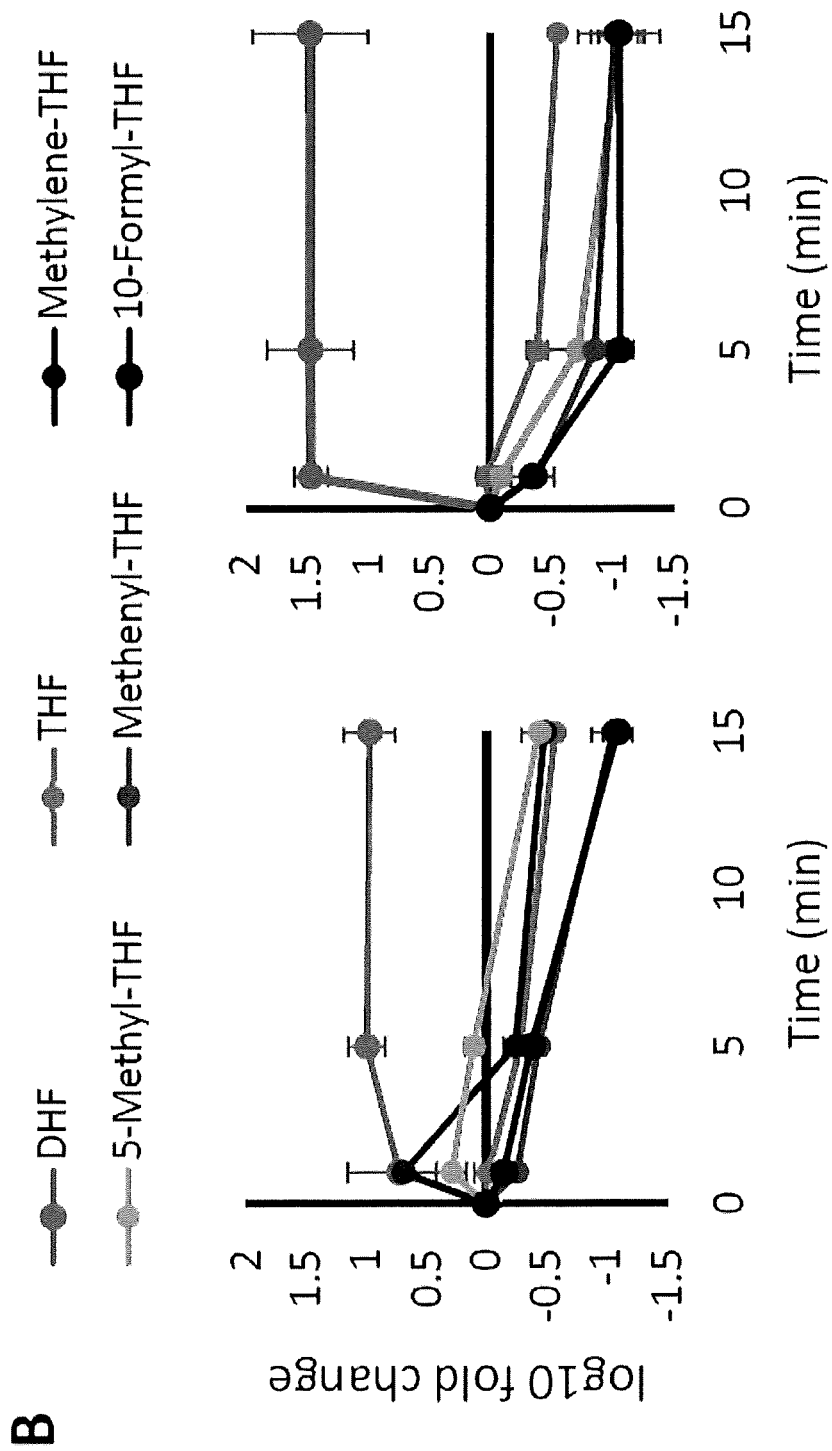
FIG. 13(B) illustrates FolA inhibition in E. coli cells treated with SCH 79797.

To investigate what aspects of folate synthesis were being altered by SCH treatment, metabolomics and mass spectrometry were performed to measure the relative abundance of folate metabolites in NCM 3722 E. coli cells treated with SCH (FIG. 13A). NCM 3722 cells were grown in Gutnick Minimal Media and treated with 1× MIC SCH (31.25 µM) for 15 minutes. It was found that in response to SCH treatment, dihydrofolate (DHF) levels rose approximately 10-fold higher over time than normal DHF levels, while the level of all other metabolites downstream of FolA dropped rapidly (FIG. 13B). This metabolic response is characteristic of FolA inhibition and was also observed when NCM 3722 cells were treated with Trimethoprim (FIG. 13B). This suggests that FolA is a potential target of SCH.

Figure 13C:
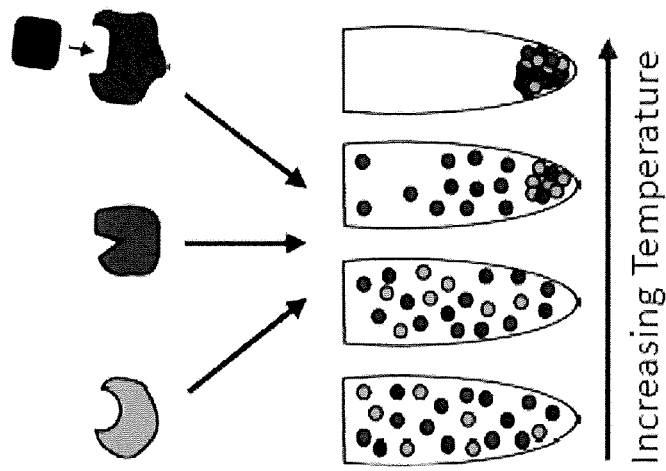
FIG. 13(C) illustrates thermal profiling performed on E. coli (lptD4213) cells.
Figure 13C:
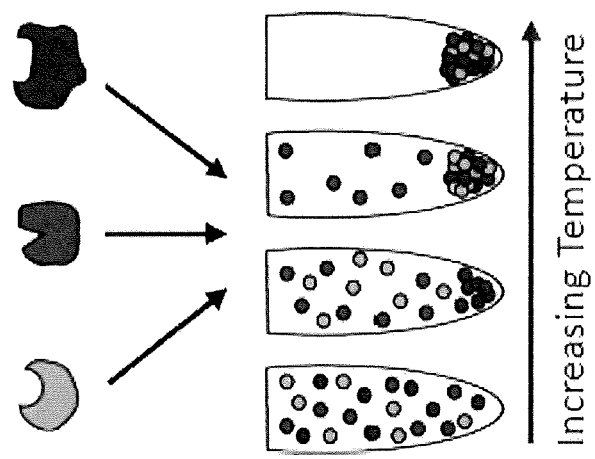
Figure 13D:
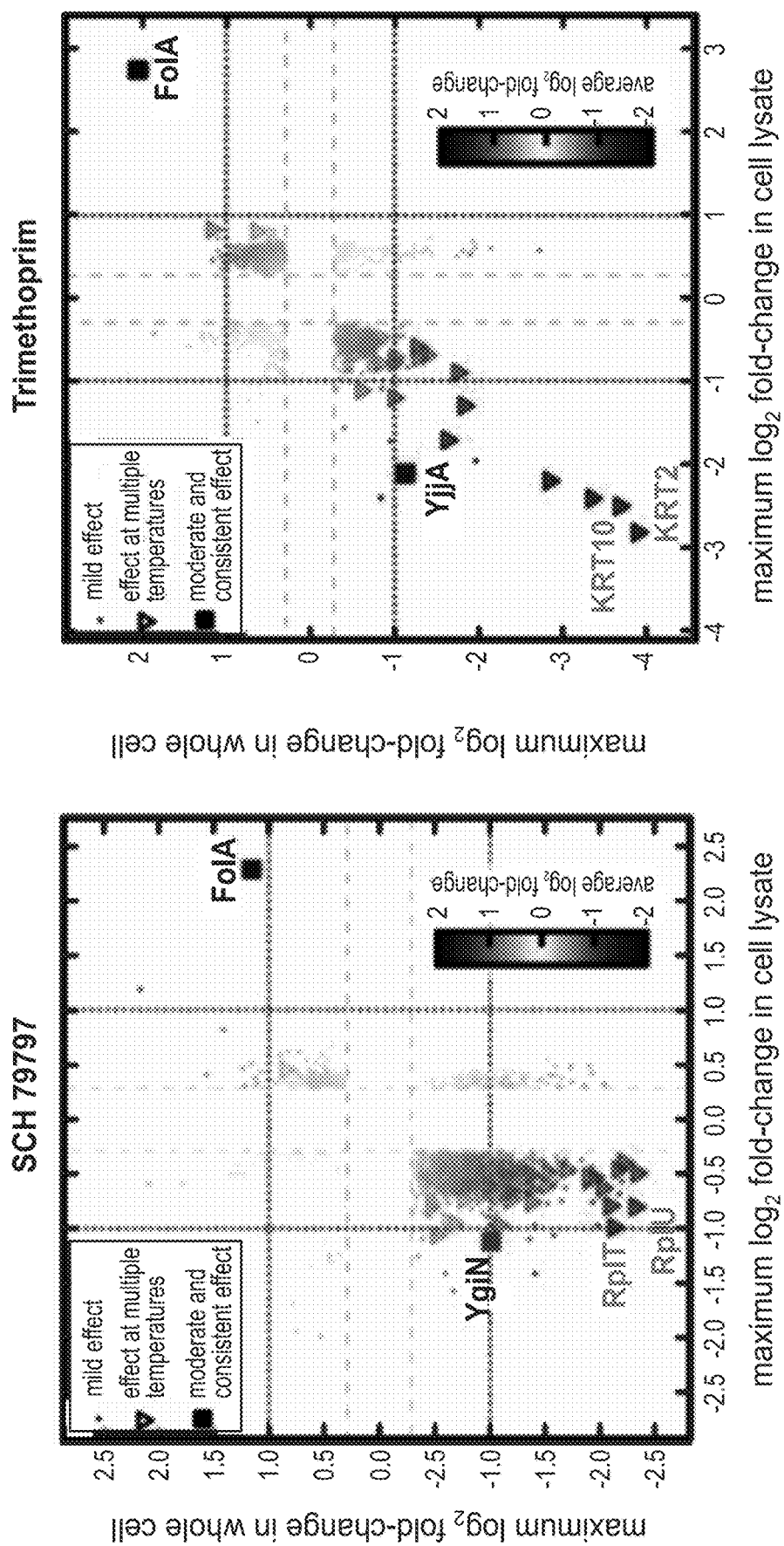
FIG. 13(D) illustrates results of thermal profiling of the E. coli (lptD4213).
Figure 13E:
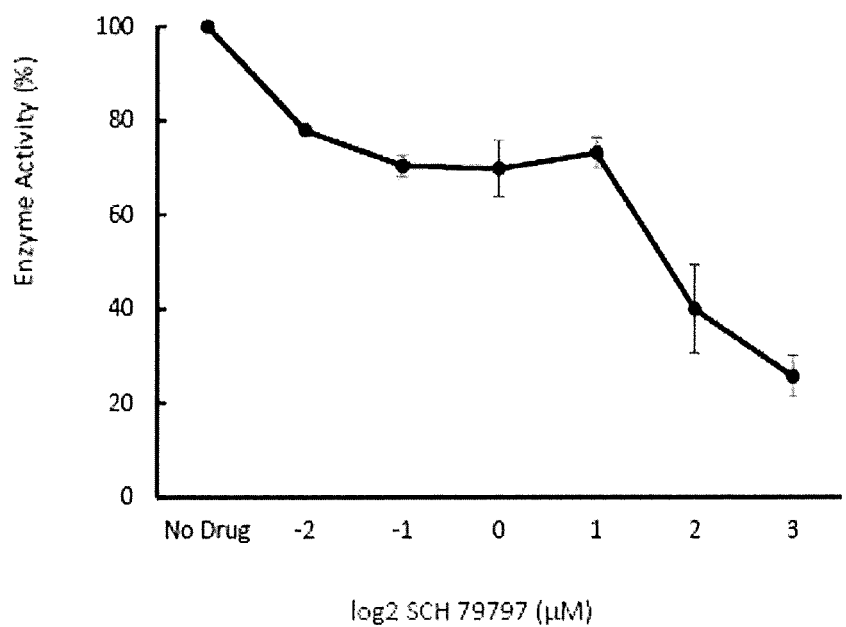
FIG. 13(E) illustrates Fol A inhibition by SCH 79797 and Trimethoprim.
Figure 13E:
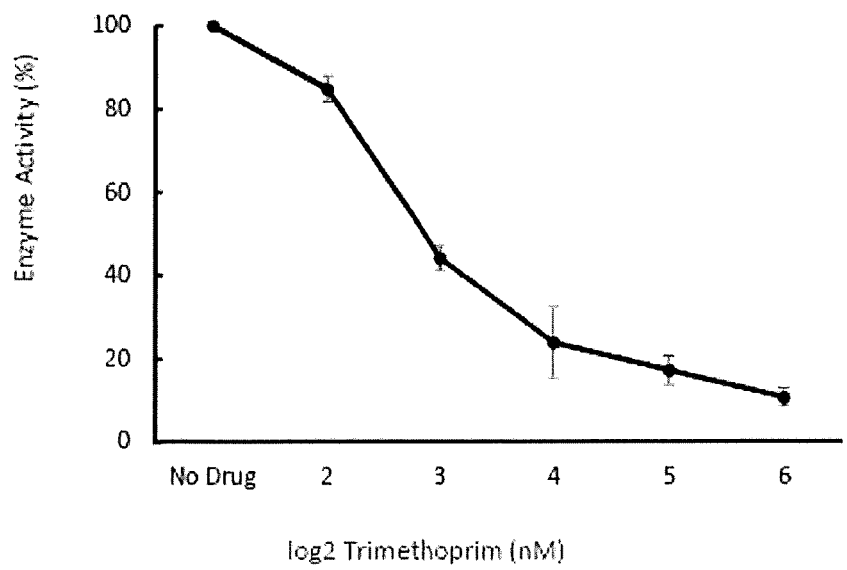

To further validate this hypothesis, thermal profiling was performed on 1ptd4213 E. coli cells (FIG. 13C). This assay measures proteome-wide changes in protein thermal stability because of small molecule binding and can be used to determine the target of small molecules. It was found that in the presence of SCH and Trimethoprim, FolA was the most stabilized under thennal stress (FIG. 13D). This further validated the hypothesis that SCH targets FolA in the cell. Lastly, the in vitro enzymatic activity of purified FolA from E. coli was measured, and it was found that both SCH and Trimethoprim inhibit FolA (FIG. 13E).

Figure 14A:
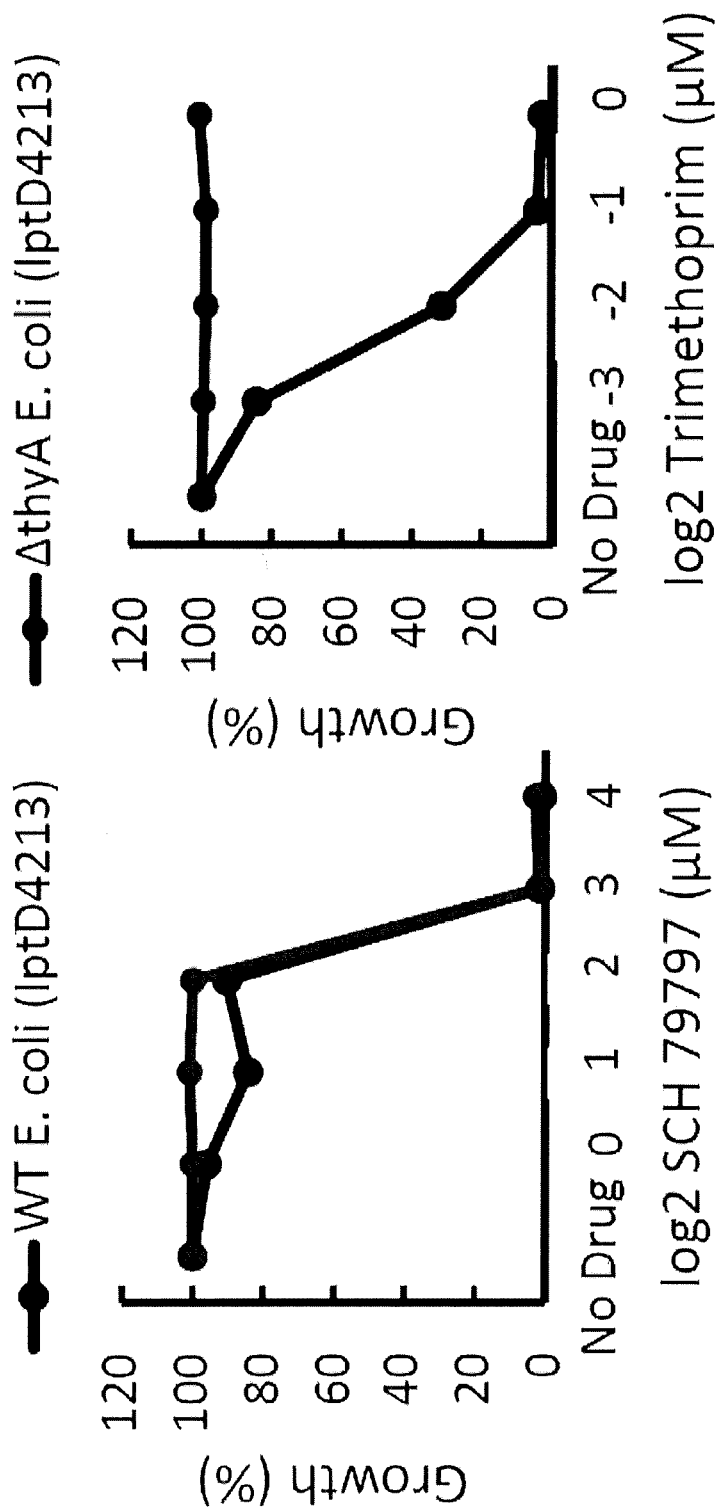
FIG. 14(A) illustrates resistance of ΔthyA E. coli 1ptD4213 cells to Trimethoprim and the lack of resistance of ΔthyA E. coli 1ptD4213 cells to SCH 79797.
Figure 14B:
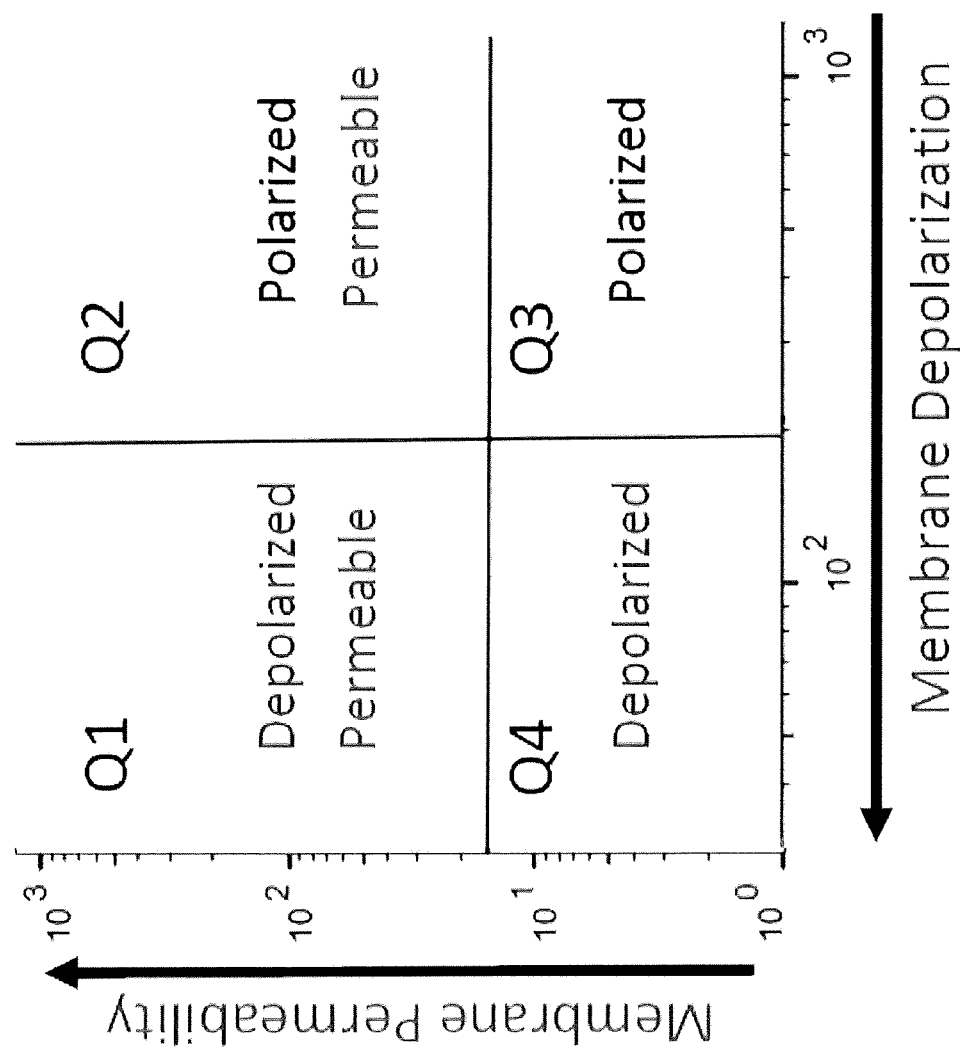
FIG. 14(B) is a grid characterizing cell membrane polarization and permeability.
Figure 14C:
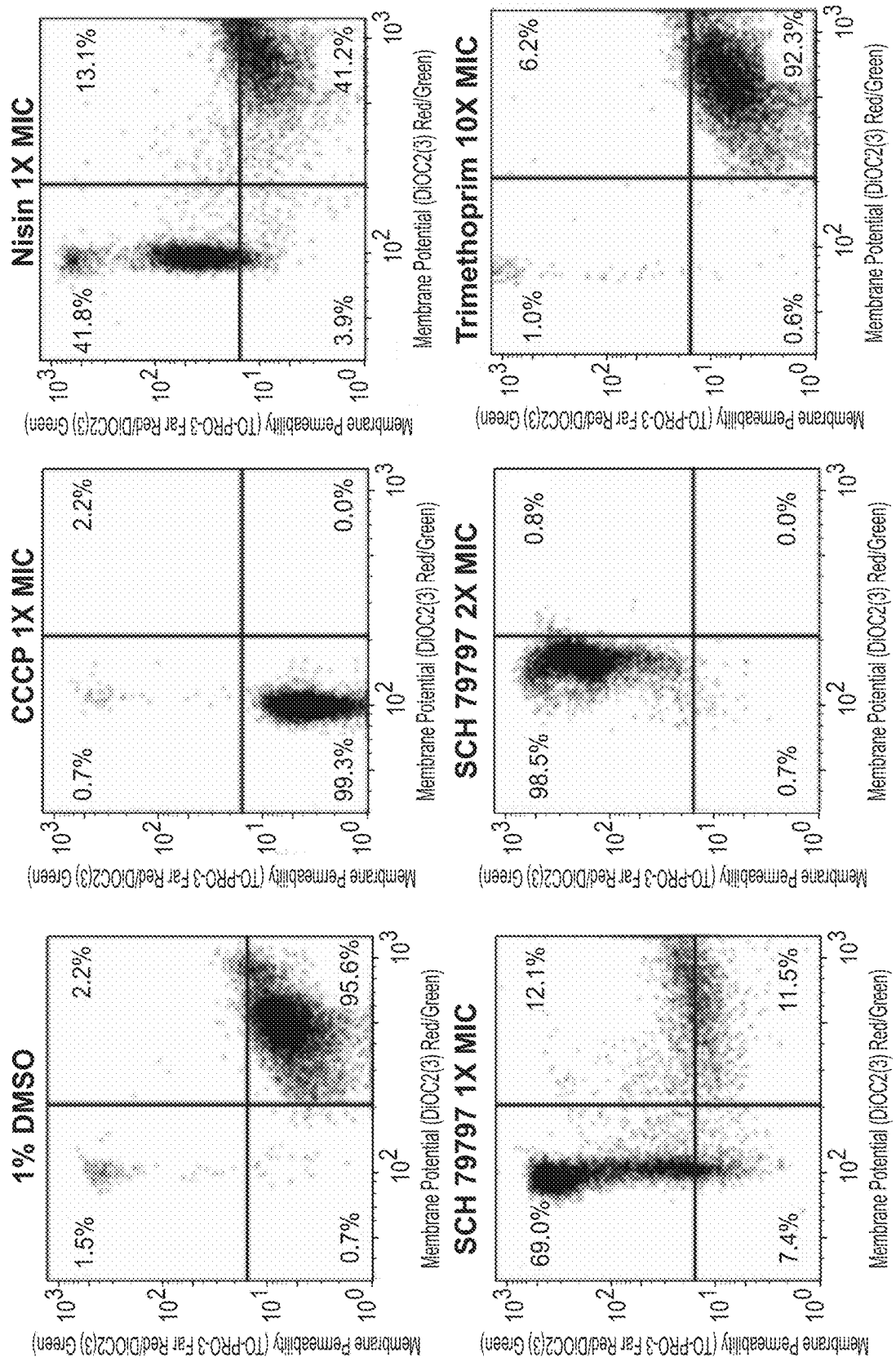
FIG. 14(C) illustrates E. coli (lptD4213) cell polarization and permeability in response to various compounds, including SCH 79797.
Figure 14D:
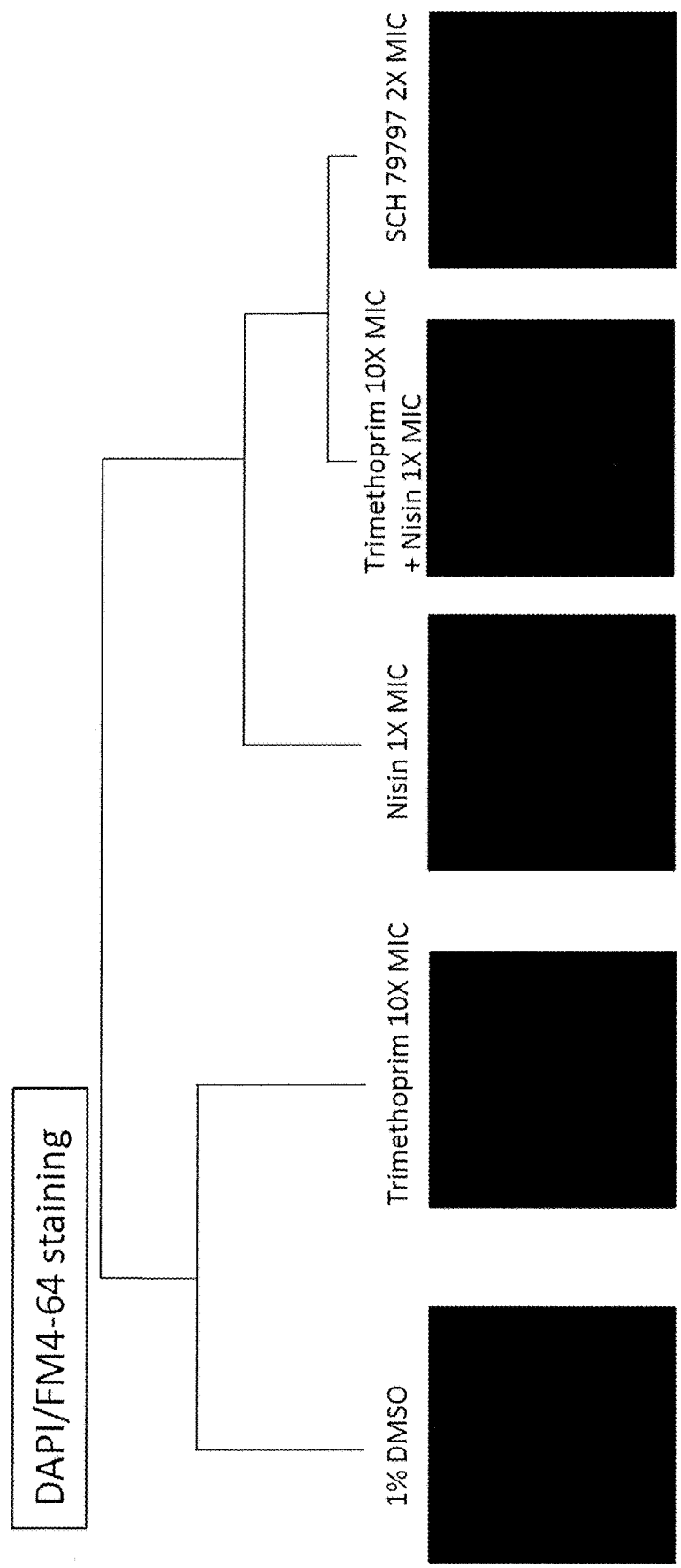
FIG. 14(D) illustrates the cytological profile of cells treated with Trimethoprim, Nisin and SCH 79797 according to some embodiments.
Figure 14E:
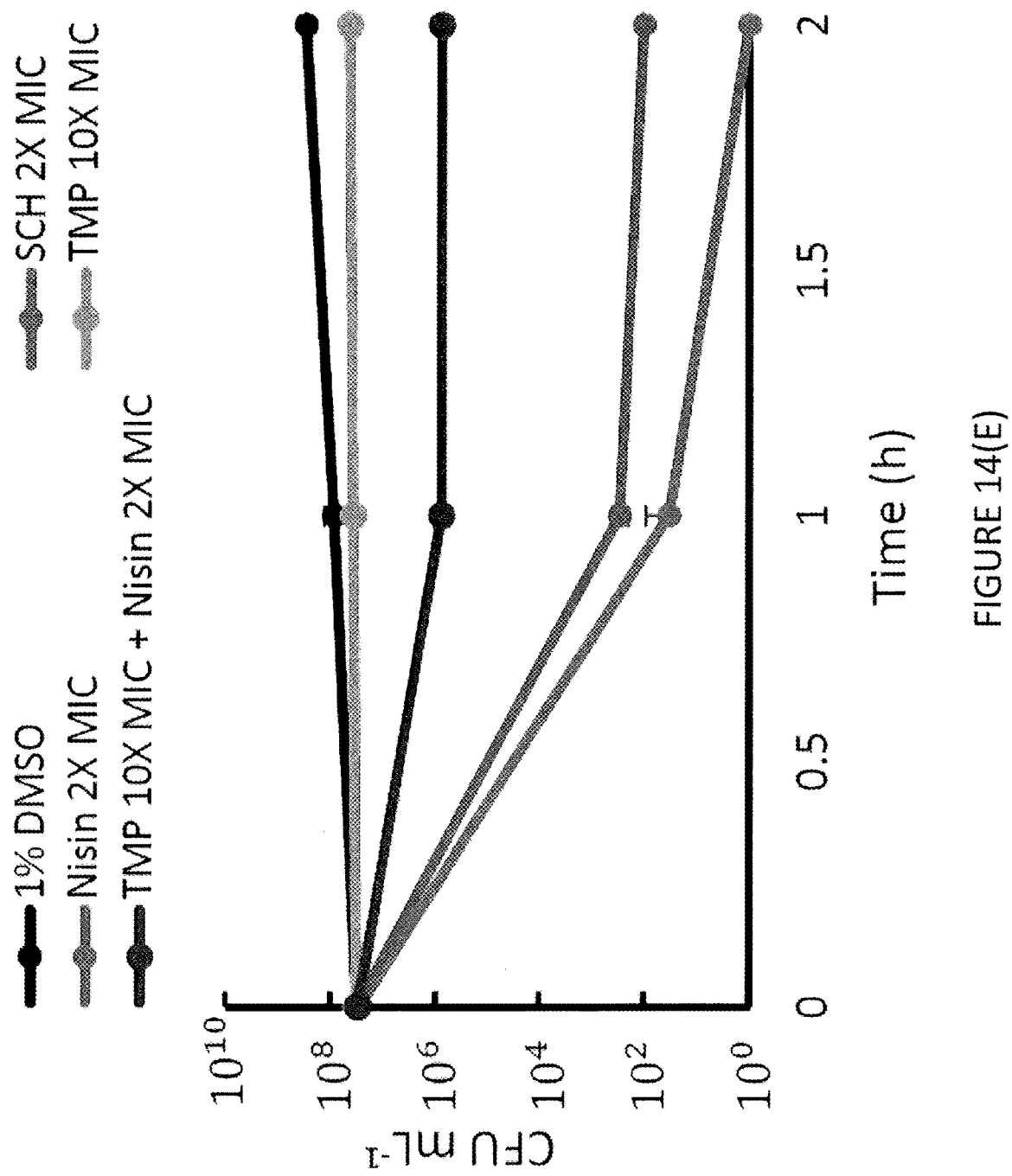
FIG. 14(E) illustrates antagonism when E. coli (lptD4213) cells are co-treated with Trimethoprim and Nisin.
Figure 14F:
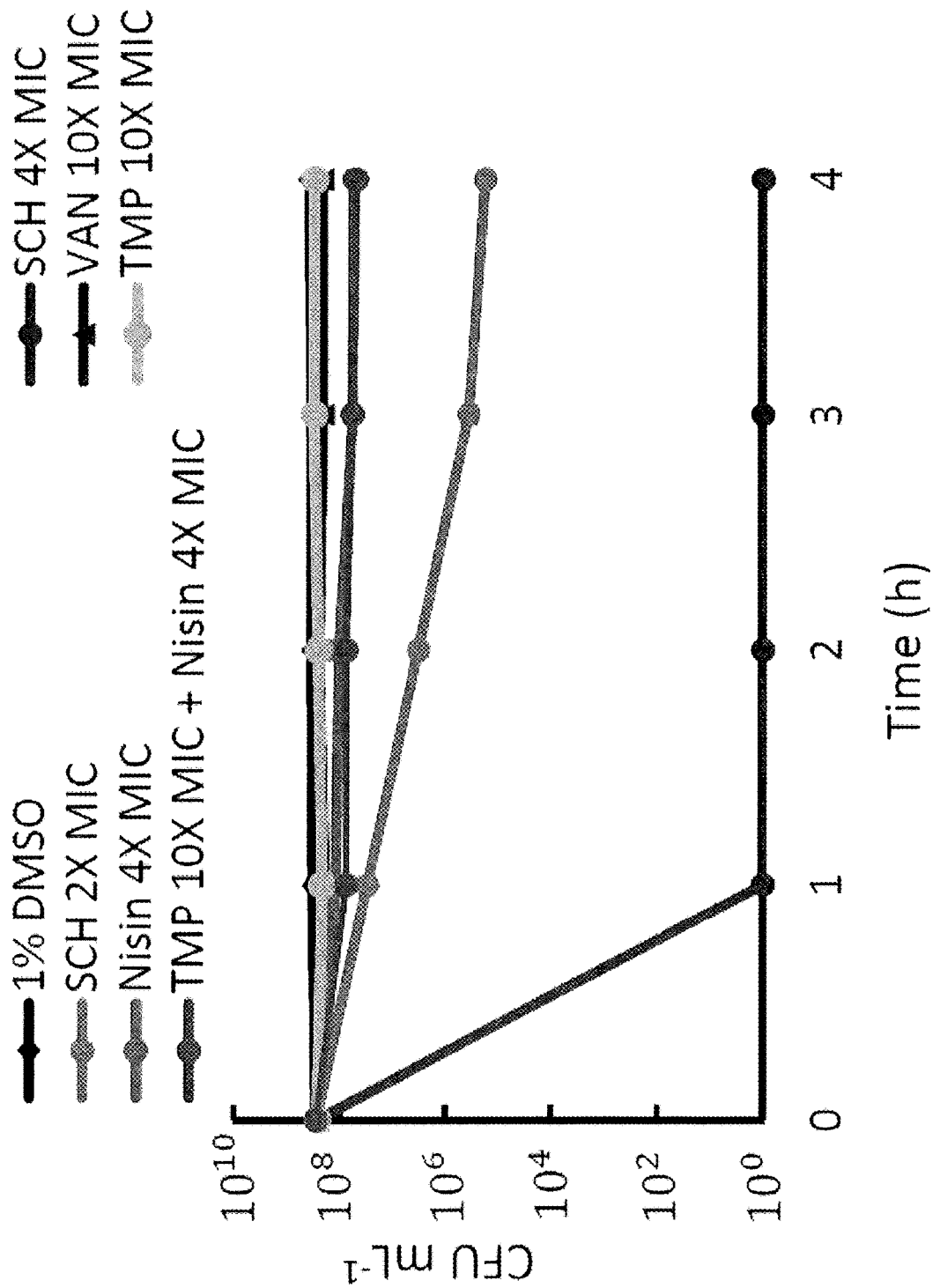
FIG. 14(F) illustrates the activity of various compounds, including SCH 79797, against USA300 MRSA persister cells.

Although SCH shares a target with Trimethoprim, these two antibiotics do not have similar phenotypes. Trimethoprim resistance is much more frequent than SCH. Additionally, previous literature has demonstrated that ΔthyA cells are resistant to antifolate drugs when supplemented with exogenous Thymine. However, ΔthyA lptD4213 cells are still susceptible SCH while resistant to high levels of Trimethoprim (FIG. 14A). To determine whether SCH has an additional target, tests were performed to see whether SCH induces membrane depolarization and/or membrane permeability. It was hypothesized that SCH may be targeting the membrane since antibiotics that target essential components of the cell, such as the membrane, do not tend to accumulate resistance easily, like SCH. To test this hypothesis, the membrane potential and membrane permeability of lptD4213 cells were measured using the fluorescent dyes, DIOC$_2$(3) and TO-PRO-3, and flow cytometry. DIOC$_2$(3) is a cationic dye that accumulates in the cytoplasm of cells with an active membrane potential and shifts its fluorescence from red to green. The dye also stains the membrane of the cells in green and as a result the ratio of the red to green signals can provide a morphology and size independent measure of membrane potential (FIG. 14B). TO-PRO-3 is a nucleic acid stain that only stains cells with compromised membranes (FIG. 14B). After 10 minutes of treatment with SCH, it was observed that unlike Trimethoprim, SCH dissipates the cell's membrane potential like the membrane depolarizing agent CCCP and induces membrane permeability (FIG. 14C). Interestingly, SCH membrane activity was similar to lantibiotic Nisin. Nisin acts by binding to the Lipid A portion of bacterial lipopolyschharides and forms pores in the bacterial cytoplasmic membrane. This causes membrane depolarization and consequent loss of metabolites and cell death. As a result, the killing profile of SCH was replicated by treating cells with the combination of the antifolate antibiotic, Trimethoprim, with the membrane disrupting antibiotic, Nisin. To measure how cells respond to antibiotic treatment, a modified version of an imaging-based method known as Bacterial Cytological Profiling (BCP) was performed. BCP allows identification of the cellular pathway(s) targeted by a small-molecule antibiotic using several parameters derived from quantitatively imaging dye-treated *E. coli* cells. Specifically, upon treatment with an antibiotic, the cells were exposed to FM4-64, which discretely stains the cell membrane, SYTOX, which reports on the permeability of the cell membrane, and DAPI, a DNA stain. Using the information derived from these fluorescent dyes, antibiotics with similar modes of action are found to cluster into specific cytological profiles based on their mechanisms of action. It was determined that the cytological profile of cells treated with both Trimethoprim and Nisin most closely resembled that of cells treated with SCH (FIG. 14D). This indicated that SCH has multiple modes of action as both an antifolate, depolarizing and permeabilization agent. Interestingly, however, when lptD4213 cells are co-treated with Trimethoprim and Nisin, antagonism is observed (FIG. 14E). A potential explanation for this is that the bacteriostatic nature of Trimethoprim protects cells from lysis due to Nisin treatment. To further test the effectiveness of SCH, we measured the activity of SCH against USA300 MRSA persister cells and observed that SCH killed MRSA persister cells at concentrations, close to the MIC of exponentially growing USA300 cells (FIG. 14F). The dual-mode of action of SCH may explain why it is difficult for bacteria to acquire resistance to SCH. Many antibiotics, such as Trimethoprim, only have one target that needs to be mutated or bypassed in order to get resistance. However, SCH targets both folate synthesis and depolarizes the cell membrane making it very difficult impossible to get resistance too. This results in the potent bactericidal activity against a broad spectrum of pathogenic bacteria.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of treating a bacterial infection comprising:
administering to a patient in need thereof a therapeutically effective amount of a compound of Formula (I) and/or salt thereof:

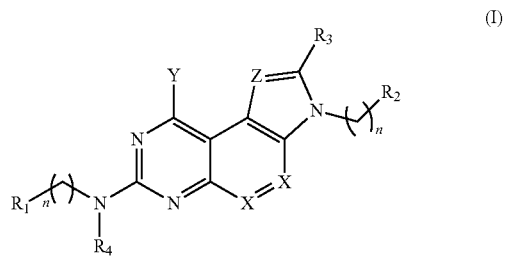

wherein $R_1$-$R_4$ are independently selected from the group consisting of hydrogen, alkyl, alkenyl, heteroalkyl, cycloalkyl, heterocycloalkyl, aryl, heteroaryl, amide, and sulfonamide, wherein the alkyl, alkenyl, heteroalkyl, cycloalkyl, heterocycloalkyl, aryl, heteroaryl, amide and sulfonamide are optionally substituted with one or more substituents selected from the group consisting of ($C_1$-$C_{10}$)-alkyl, cycloalkyl, alkoxy, halo, and hydroxy; and wherein X and Z are independently selected from the group consisting of C, N and O; and wherein Y is selected from the group consisting of OH and $NR_9R_{10}$, wherein $R_9$ and $R_{10}$ are independently selected from the group consisting of hydrogen, alkyl, cycloalkyl, and aryl, and wherein $R_9$ and $R_{10}$ may optionally form a ring structure; and n is an integer from 0 to 5.

2. The method of claim 1, wherein bacteria of the infection are gram negative.

3. The method of claim 1, wherein bacteria of the infection are gram positive.

4. The method of claim 1, wherein the bacterial infection is resistant to one or more antibiotic compounds differing from the compound of Formula 1.

5. The method of claim 1, wherein the compound of Formula (I) is administered at a concentration of 0.1 μg/ml to 100 μg/ml.

6. The method of claim 1, wherein the compound of Formula (I) exhibits more than one target for antibacterial activity.

7. The method of claim 6, wherein the compound of Formula (I) targets bacterial folate metabolism.

8. The method of claim 7, wherein the compound of Formula (I) targets membrane polarization and/or membrane permeability.

9. The method of claim 1, wherein $R_1$ is selected from the group consisting of cycloalkyl and heterocycloalkyl and $R_2$ is selected from the group consisting of alkyl, cycloalkyl, heterocycloalkyl, aryl and heteroaryl.

10. The method of claim 1, wherein the bacterial infection comprises *A. baumanii*.

11. The method of claim 1, wherein the compound of Formula (I) and/or salt thereof is:

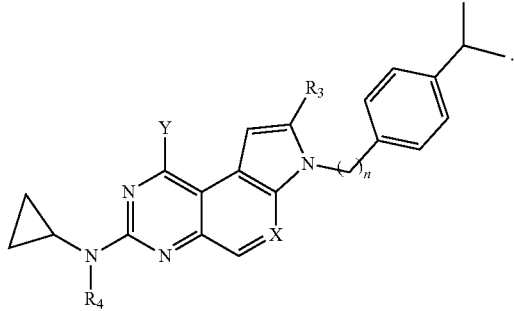

12. The method of claim 11, wherein the compound of Formula (I) and/or salt thereof is:

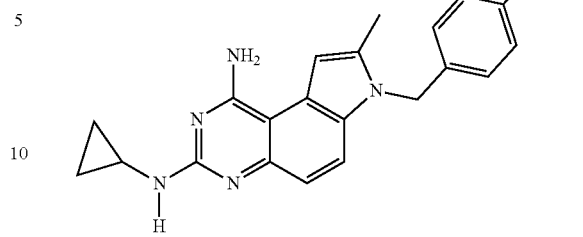

13. The method of claim 12, wherein the compound of Formula (I) and/or salt thereof is administered at a concentration of 0.1 µg/ml to 100 µg/ml.

14. The method of claim 12, wherein the compound of Formula (I) and/or salt thereof targets bacterial folate metabolism.

* * * * *